US008263079B2

(12) United States Patent
Doody et al.

(10) Patent No.: US 8,263,079 B2
(45) Date of Patent: Sep. 11, 2012

(54) ANTIBODIES AGAINST CSF-1R

(75) Inventors: Jacqueline Francoise Doody, Ozone Park, NY (US); Yanxia Li, Floral Park, NY (US)

(73) Assignee: ImClone, LLC, Indianapolis, IN (US)

( * ) Notice: Subject to any disclaimer, the term of this patent is extended or adjusted under 35 U.S.C. 154(b) by 43 days.

(21) Appl. No.: 13/073,004

(22) Filed: Mar. 28, 2011

(65) Prior Publication Data

US 2011/0243947 A1    Oct. 6, 2011

Related U.S. Application Data

(60) Provisional application No. 61/319,896, filed on Apr. 1, 2010.

(51) Int. Cl.
*A61K 39/395* (2006.01)
*C12P 21/08* (2006.01)
(52) U.S. Cl. .................................. 424/143.1; 424/142.1
(58) Field of Classification Search .................. None
See application file for complete search history.

(56) References Cited

FOREIGN PATENT DOCUMENTS

| EP | 239400 | 9/1987 |
|---|---|---|
| EP | 332424 | 9/1989 |
| EP | 338745 | 10/1989 |
| JP | 09067400 | 3/1997 |
| WO | 89/09622 | 10/1989 |
| WO | 2004/045532 | 3/2004 |
| WO | 2009/026303 | 2/2009 |
| WO | 2009/112245 | 9/2009 |
| WO | 2006/096461 | 2/2011 |

OTHER PUBLICATIONS

Burns CJ, Wilks AF. c-FMS inhibitors: a patent review. Expert Opin Ther Pat. Feb. 2011;21(2):147-65. Epub Jan. 5, 2011.*
Aharinejad, et al., Colony-Stimulating Factor-1 Blockade by Antisense Oligonucleotides and Small Interfering RNAs Suppresses Growth of Human Mammary Tumor Xenografts in Mice, Cancer Research 62(18):5317-5324 (2002).
Bourette, et al., Early Events in M-CSF Receptor Signaling, Growth Factors 17:155-166 (2000).
Burdon, et al. eds., Laboratory Techniques in Biochemistry and Molecular Biology, vol. 13 (Elsevier Science Publishers, Amsterdam) in Monoclonal Antibody Technology, The Production and Characterization of Rodent and Human Hybridomas (Campbell ed., 1984).
Coligan, et al., Current Protocols in Immunology, Wiley & Sons, Inc. (2007).
Coussens, et al., Structural alteration of viral homologue or receptor proto-oncogene fms at carboxyl terminus, Nature 320:277-280 (1986).
Dubreuil, et al., c-fms Expression is a Molecular Marker of Human Acute Myeloid Leukemias, Blood 72 (3):1081-1085 (1988).
Gerharz, et al., Secretion of GM-CSF and M-CSF by Human Renal Cell Carcinomas of Different Histologic Types, Urol. 58(5):821-827 (2001).
Goswami, et al., Macrophages Promote the Invasion of Breast Carcinoma Cells via a Colony-Stimulating Factor-1/Epidermal Growth Factor Paracrine Loop, Cancer Res 65(12)_5278-5283 (2005).
Hawkins, et al., Selection of Phage Antibodies by Binding Affinity Mimicking Affinity Maturation, J. Mol. Biol. 226:889-896 (1992).
Huse, et al., Generation of a Large Combinatorial Library of the Immunoglobulin Repertoire in Phage Lambda, Science 246:1275-1281 (1989).
Kabat, et al., Attempts to Locate Complementarity-Determining Residues in the Variable Positions of Light and Heavy Chains, Ann. NY Acad. Sci. 190:382-393 (1971).
Kabat, et al., Sequences of Proteins of Immunological Interest, Fifth Edition, U.S. Department of Health and Human Services, NIH Publication No. 91-3242 (1991).
Kacinski, et al., FMS (CSF-1 receptor) and CSF-1 transcripts and protein are expressed by human breast carcinomas in vivo and in vitro, Oncogene 6(6):941-952 (1991).
Kaufmann, et al., Amplification and Expression of Sequences Cotransfected with a Modular Dihydrofolate Reductase Complementary DNA Gene, J. Mol. Biol. 159:601-621 (1982).
Kawakami, et al., Macrophage-colony stimulating factor inhibits the growth of human ovarian cancer cells in vitro, Eur J. Cancer 36(15):1991-1997 (2000).
Kirma, et al., Overexpression of the Colony-Stimulating Factor )CSF-1) and/or Its Receptor c-fms in Mammary Glands of Transgenic Mice Results in Hyperplasia and Tumor Formation, Cancer Research 64(12):4162-4170 (2004).
Kohler, et al., Continuous cultures of fused cells secreting antibody of predefined specificity, Nature 256:495-497 (1975).
Lamoyi, et al., Preparation of F(ab')2 Fragments from Mouse IgG of Various Subclasses, J. Immunol. Methods 56:235-243 (1983).
Lawicki, et al., The pretreatment plasma level and diagnostic utility of M-CSF in benign breast tumor and breast cancer patients, Clinica Chimica Acta; International Journal of Clinical Chemistry 371(1-2):112-116 (2006).
Lin, et al., Discovery of a Cytokine and Its Receptor by Functional Screening of the Extracellular Proteome, Science 320:807-811 (2008).
Low, et al., Mimicking Somatic Hypermutation: Affinity Maturation of Antibodies Displayed on Bacteriophage Using a Bacterial Mutator Strain, J. Mol. Biol., 250:359-368 (1996).

(Continued)

*Primary Examiner* — David Romeo
(74) *Attorney, Agent, or Firm* — Nicole S. Woods

(57) ABSTRACT

The invention provides a human antibody that binds human CSF-1R with high affinity. Antibodies of the present invention have significant advantages over the antibodies known in the art by being multifunctional: inhibiting signaling of CSF-1R, internalizing and inducing CSF-1R degradation and stimulating ADCC in cell including tumors, macrophages and monocytes. They are also shown to be effective in treating leukemia, breast, endometrial and prostate cancer alone or in combination with docetaxel, paclitaxel, Herceptin® or doxorubicin.

13 Claims, No Drawings

OTHER PUBLICATIONS

Mroczko, et al., Serum macrophage-colony stimulating factor levels in colorectal cancer patients correlate with lymph node metastasis and poor prognosis, Clin. Chim. Acta 380(1-2) 208-212 (2007).

Parham, on the Fragmentation of Monoclonal IgG1, IgG2a, and IgG2b from BALB/c Mice, J. Immunol. 131:2895-2902 (1983).

Paulus, et al., Colony-Stimulating Factor-1 Antibody Reverses Chemoresistance in Human MCF-7 Breast Cancer Xenografts, Cancer Res. 66(8):4349-4356 (2006).

Pixley, et al., CSF-1 regulation of the wandering macrophage: complexity in action, Trends in Cell Biology 14 (11):628-638 (2004).

Pollard, et al., Tumor-educated macrophages promote tumour progression and metastasis, Nat Rev Cancer 4 (1):71-78 (2004).

Qian, et al., Macrophage Diversity Enhances Tumor Progression and Metastasis, Cell 141:39-51 (2010).

Rao, et al., Membrane-Bound Macrophage Colony-Stimulating Factor Mediated Auto-Juxtacrine Downregulates Matrix Metalloproteinase-9 Release on J6-1 Leukemic Cell, Exp Biol. Med. 229(9):946-953 (2004).

Remenigton: The Science and Practice of Pharmacy (A. Gennaro, et al., eds., 19th ed., Mack Publishing Co., 1995).

Sambrook, et al., Molecular Cloning: A Laboratory Manual, 2nd ed., Cold Spring Harbor Laboratory Press (1989).

Scahill. et al., Expression and characterization of the product of a human immune interferon cDNA gene in Chinese hamster ovary cells, Proc. Nat'l Acad. Sci. USA 80:4654-4659 (1983).

Sherr, et al., Inhibition of Colony-Stimulating Factor-1 Activity by Monoclonal Antibodies to the Human CSF-1 Receptor, Blood 73(7):1786-1793 (1989).

Soares, et al., CSF1R copy number changes, point mutations, and RNA and protein overexpression in renal cell carcinomas, Modern Pathol. 22:744-752 (2009).

Southern, et al., Transformation of Mammalian Cells to Antibiotic Resistance with a Bacterial Gene Under Control of the SV40 Early Region Promoter, J. Mol. Appl. Genet. 1:327-341 (1982).

Steidl, et al., Tumor-Associated Macrophages and Survival in Classic Hodgkin's Lymphoma, New Engl. J. Med. 362 (10):875-885 (2010).

Subramani, et al. Expression of the Mouse Dihydrofolate Reductase Complementary Deoxyribonucleic Acid in Simian Virus 40 Vectors, Mol. Cell. Biol. 1:854-864 (1981).

Toy, et al., The Activated Macrophage Colony-Stimulating Factor (CSF-1) Receptor as a Predictor of Poor Outcome in Advanced Epithelial Ovarian Carcinoma, Gynecologic Oncology 80(2):194-200 (2001).

Urlaub, et al., Isolation of Chinese hamster cell mutants deficient in dihydrofolate reductase activity, Proc. Nat'l Acad. Sci. USA 77:4216-4220 (1980).

Wang, et al., Identification of the Ligand-Binding Regions in the Macrophage Colony-Stimulating Factor Receptor Extracellular Domain, Mol. Cell. Biol. 13(9):5348-5359 (1993).

Yang, et al., CDR Walking Mutagenesis for the Affinity Maturation of a Potent Human Anti-HIV-1 Antibody into the Picomolar Range, J. Mol. Biol. 254:392-403 (1995).

Zhang, et al., Combining multiple serum tumor markers improves detection of stage I epithelial ovarian cancer, Gyn. Oncol. 107(3):526-531 (2007).

Zheng, et al., Macrophages are an abundant component of myeloma microenvironment and protect myeloma cells from chemotherapy drug-induced apoptosis, Blood 114:3625-3628 (2009).

Zheng, et al., Membrane-bound macrophage colony-stimulating factor and its receptor play adhesion molecule-like roles in leukemic cells, Lukemia Res. 24:375-383 (2000).

Zhu, et al., High Expression of Macrophage Colony-Stimulating Factor in Peritumoral Liver Tissue is Associated With Poor Survival After Curative Resection of Hepatocellular Carcinoma, J. Clin. Oncol. 26:2707-2716 (2008).

Reslan, et al., Understanding and circumventing resistance to anticancer monoclonal antibodies, MAbs 1(3):222-229 (2009).

* cited by examiner

SEQUENCE LISTING

<160> NUMBER OF SEQ IDS NOS: 18

<210> SEQ ID NO 1
<211> LENGTH: 5
<212> TYPE: PRT
<213> ORGANISM: Artificial sequence
<220> FEATURE:
<223> OTHER INFORMATION: Synthetic construct

<400> SEQUENCE: 1

Ser Tyr Gly Met His
1               5

<210> SEQ ID NO 2
<211> LENGTH: 17
<212> TYPE: PRT
<213> ORGANISM: Artificial sequence
<220> FEATURE:

```
<223> OTHER INFORMATION: Synthetic construct

<400> SEQUENCE: 2

Val Ile Trp Tyr Asp Gly Ser Asn Lys Tyr Tyr Ala Asp Ser Val Lys
1               5                   10                  15

Gly

<210> SEQ ID NO 3
<211> LENGTH: 11
<212> TYPE: PRT
<213> ORGANISM: Artificial sequence
<220> FEATURE:
<223> OTHER INFORMATION: Synthetic construct

<400> SEQUENCE: 3

Gly Asp Tyr Glu Val Asp Tyr Gly Met Asp Val
1               5                   10

<210> SEQ ID NO 4
<211> LENGTH: 11
<212> TYPE: PRT
<213> ORGANISM: Artificial sequence
<220> FEATURE:
<223> OTHER INFORMATION: Synthetic construct

<400> SEQUENCE: 4

Arg Ala Ser Gln Gly Ile Ser Asn Ala Leu Ala
1               5                   10

<210> SEQ ID NO 5
<211> LENGTH: 7
<212> TYPE: PRT
<213> ORGANISM: Artificial sequence
<220> FEATURE:
<223> OTHER INFORMATION: Synthetic construct

<400> SEQUENCE: 5

Asp Ala Ser Ser Leu Glu Ser
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic construct

<400> SEQUENCE: 6

Gln Gln Phe Asn Ser Tyr Pro Trp Thr
1               5

<210> SEQ ID NO 7
<211> LENGTH: 120
<212> TYPE: PRT
<213> ORGANISM: Artificial sequence
<220> FEATURE:
<223> OTHER INFORMATION: Synthetic construct

<400> SEQUENCE: 7

Gln Asp Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45
```

```
Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Asp Tyr Glu Val Asp Tyr Gly Met Asp Val Trp Gly Gln
               100                 105                 110

Gly Thr Thr Val Thr Val Ala Ser
               115                 120

<210> SEQ ID NO 8
<211> LENGTH: 107
<212> TYPE: PRT
<213> ORGANISM: Artificial sequence
<220> FEATURE:
<223> OTHER INFORMATION: Synthetic construct

<400> SEQUENCE: 8

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Trp
                85                  90                  95

Thr Phe Gly Gln Gly Thr Lys Val Glu Ile Lys
               100                 105

<210> SEQ ID NO 9
<211> LENGTH: 450
<212> TYPE: PRT
<213> ORGANISM: Artificial sequence
<220> FEATURE:
<223> OTHER INFORMATION: Synthetic construct

<400> SEQUENCE: 9

Gln Asp Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Glu Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Asp Tyr Glu Val Asp Tyr Gly Met Asp Val Trp Gly Gln
               100                 105                 110

Gly Thr Thr Val Thr Val Ala Ser Ala Ser Thr Lys Gly Pro Ser Val
               115                 120                 125
```

```
Phe Pro Leu Ala Pro Ser Ser Lys Ser Thr Ser Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 10
<211> LENGTH: 214
<212> TYPE: PRT
<213> ORGANISM: Artificial sequence
<220> FEATURE:
<223> OTHER INFORMATION: Synthetic construct

<400> SEQUENCE: 10

Ala Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Ser Asn Ala
            20                  25                  30
Leu Ala Trp Tyr Gln Gln Lys Pro Gly Lys Ala Pro Lys Leu Leu Ile
```

```
                35                  40                  45
Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 469
<212> TYPE: PRT
<213> ORGANISM: Artificial sequence
<220> FEATURE:
<223> OTHER INFORMATION: Synthetic construct

<400> SEQUENCE: 11

Met Gly Trp Ser Cys Ile Ile Leu Phe Leu Val Ala Thr Ala Thr Gly
  1               5                  10                  15

Val His Ser Gln Asp Gln Leu Val Glu Ser Gly Gly Gly Val Val Gln
             20                  25                  30

Pro Gly Arg Ser Leu Arg Leu Ser Cys Ala Ala Ser Gly Phe Thr Phe
         35                  40                  45

Ser Ser Tyr Gly Met His Trp Val Arg Gln Ala Pro Gly Glu Gly Leu
 50                  55                  60

Glu Trp Val Ala Val Ile Trp Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Gly Asp Tyr Glu Val Asp Tyr Gly Met Asp Val
        115                 120                 125

Trp Gly Gln Gly Thr Thr Val Thr Val Ala Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190
```

```
Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465

<210> SEQ ID NO 12
<211> LENGTH: 233
<212> TYPE: PRT
<213> ORGANISM: Artificial sequence
<220> FEATURE:
<223> OTHER INFORMATION: Synthetic construct

<400> SEQUENCE: 12

Met Gly Trp Ser Cys Ile Ile Leu Phe Leu Val Ala Thr Ala Thr Gly
1               5                   10                  15

Val His Ser Ala Ile Gln Leu Thr Gln Ser Pro Ser Ser Leu Ser Ala
            20                  25                  30

Ser Val Gly Asp Arg Val Thr Ile Thr Cys Arg Ala Ser Gln Gly Ile
            35                  40                  45

Ser Asn Ala Leu Ala Trp Tyr Gln Gln Lys Pro Gly Lys Ala Pro Lys
            50                  55                  60

Leu Leu Ile Tyr Asp Ala Ser Ser Leu Glu Ser Gly Val Pro Ser Arg
65                  70                  75                  80
```

```
Phe Ser Gly Ser Gly Ser Gly Thr Asp Phe Thr Leu Thr Ile Ser Ser
                85                  90                  95
Leu Gln Pro Glu Asp Phe Ala Thr Tyr Tyr Cys Gln Gln Phe Asn Ser
            100                 105                 110
Tyr Pro Trp Thr Phe Gly Gln Gly Thr Lys Val Glu Ile Lys Arg Thr
        115                 120                 125
Val Ala Ala Pro Ser Val Phe Ile Phe Pro Pro Ser Asp Glu Gln Leu
    130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys
225                 230
```

<210> SEQ ID NO 13
<211> LENGTH: 1407
<212> TYPE: DNA
<213> ORGANISM: Artificial sequence
<220> FEATURE:
<223> OTHER INFORMATION: Synthetic construct

<400> SEQUENCE: 13

```
atgggatggt catgtatcat cctttttctg gtagcaactg caactggagt acattcacag      60
gaccagctgg tggagtctgg gggaggcgtg gtccagcctg gaggtccct gagactctcc     120 tgtgcagcgt ctggattcac cttcagtagc tatggcatgc actgggtccg ccaggctcca     180
ggcgaggggc tggagtgggt ggcagttata tggtatgatg gaagtaataa atactatgca     240
gactccgtga agggccgatt caccatctcc agagacaatt ccaagaacac actgtatctg     300
caaatgaaca gcctgagagc cgaggacacg gctgtgtatt actgtgcgag aggtgactac     360
gaggtcgact acggaatgga cgtctggggc caagggacca cggtcaccgt cgcctcagct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagagagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtat     900
gtggacggcg tggaggtgca taatgccaag acaaagccgc gggaggagca gtacaacagc     960
acgtaccgtg tggtcagcgt cctcaccgtc ctgcaccaag actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aagtcagcct gacctgcctg gtcaaaggct tctatcccag cgacatcgcc    1200
```

```
gtggagtggg agagcaatgg gcagccggag aacaactaca agaccacgcc tcccgtgctg    1260
gactccgacg gctccttctt cctctattcc aagctcaccg tggacaagag caggtggcag    1320
caggggaacg tcttctcatg ctccgtgatg catgaggctc tgcacaacca ctacacgcag    1380
aagagcctct ccctgtctcc gggcaaa                                        1407

<210> SEQ ID NO 14
<211> LENGTH: 838
<212> TYPE: DNA
<213> ORGANISM: Artificial sequence
<220> FEATURE:
<223> OTHER INFORMATION: Synthetic construct

<400> SEQUENCE: 14
atgggatggt catgtatcat ccttttcta gtagcaactg caactggagt acattcagcc      60
atccagttga cccagtctcc atcctccctg tctgcatctg taggagacag agtcaccatc    120
acttgccggg caagtcaggg cattagcaat gctttagcct ggtatcagca gaaaccaggg    180
aaagctccta agctcctgat ctatgatgcc tccagtttgg aaagtggggt cccatcaagg    240
ttcagcggca gtggatctgg gacagatttc actctcacca tcagcagcct gcagcctgaa    300
gattttgcaa cttattactg tcaacagttt aatagttacc cgtggacgtt cggccaaggg    360
accaaggtgg aaatcaaacg tgagttctag aggatccatc tgggataagc atgctgtttt    420
ctgtctgtcc ctaacatgcc ctgtgattat ccgcaaacaa cacacccaag gcagaacttt    480 gttacttaa acaccatcct gtttgcttct ttcctcagga actgtggctg caccatctgt    540
cttcatcttc ccgccatctg atgagcagtt gaaatctgga actgcctctg ttgtgtgcct    600
gctgaataac ttctatccca gagaggccaa agtacagtgg aaggtggata acgcctcca    660 atcgggtaac tcccaggaga gtgtcacaga gcaggacagc aaggacagca cctacagcct    720
cagcagcacc ctgacgctga gcaaagcaga ctacgagaaa cacaaagtct acgcctgcga    780
agtcacccat cagggcctga gctcgcccgt cacaaagagc ttcaacaggg gagagtgt     838

<210> SEQ ID NO 15
<211> LENGTH: 972
<212> TYPE: PRT
<213> ORGANISM: Artificial Sequence
<220> FEATURE:
<223> OTHER INFORMATION: Synthetic construct

<400> SEQUENCE: 15

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Ala Ser Pro His Trp Thr Leu Tyr Ser Asp Gly
        50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125
```

-continued

```
Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
530                 535                 540

Lys Tyr Gln Val Arg Trp Lys Ile Ile Glu Ser Tyr Glu Gly Asn Ser
545                 550                 555                 560
```

```
Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

<210> SEQ ID NO 16
<211> LENGTH: 972
<212> TYPE: PRT
<213> ORGANISM: Homo sapiens

<400> SEQUENCE: 16

```
Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
```

-continued

```
            385                 390                 395                 400
Pro Pro Glu Val Ser Val Ile Trp Thr Phe Ile Asn Gly Ser Gly Thr
                    405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
            435                 440                 445

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Phe Leu Phe Thr Pro Val Val Ala Cys Met Ser Ile Met Ala Leu
            515                 520                 525

Leu Leu Leu Leu Leu Leu Leu Leu Tyr Lys Tyr Lys Gln Lys Pro
        530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
                580                 585                 590

Phe Gly Lys Val Val Glu Ala Thr Ala Phe Gly Leu Gly Lys Glu Asp
            595                 600                 605

Ala Val Leu Lys Val Ala Val Lys Met Leu Lys Ser Thr Ala His Ala
610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
                660                 665                 670

Asn Phe Leu Arg Arg Lys Ala Glu Ala Met Leu Gly Pro Ser Leu Ser
            675                 680                 685

Pro Gly Gln Asp Pro Glu Gly Gly Val Asp Tyr Lys Asn Ile His Leu
690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
            770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815
```

```
Leu Pro Val Lys Trp Met Ala Pro Glu Ser Ile Phe Asp Cys Val Tyr
        820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
        850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
                900                 905                 910

Gln Ala Gln Glu Asp Arg Arg Glu Arg Asp Tyr Thr Asn Leu Pro Ser
                915                 920                 925

Ser Arg Ser Gly Gly Ser Gly Ser Ser Ser Glu Leu Glu Glu
        930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970

<210> SEQ ID NO 17
<211> LENGTH: 554
<212> TYPE: PRT
<213> ORGANISM: Homo sapiens

<400> SEQUENCE: 17

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
                100                 105                 110

Gln Glu Leu Ser Leu Arg Leu Lys Ser Cys Phe Thr Lys Asp Tyr Glu
            115                 120                 125

Glu His Asp Lys Ala Cys Val Arg Thr Phe Tyr Glu Thr Pro Leu Gln
        130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
                180                 185                 190

Tyr Pro Lys Ala Ile Pro Ser Ser Asp Pro Ala Ser Val Ser Pro His
            195                 200                 205

Gln Pro Leu Ala Pro Ser Met Ala Pro Val Ala Gly Leu Thr Trp Glu
        210                 215                 220
```

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
            245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
            275                 280                 285

Pro Gly Met Glu Asp Ile Leu Asp Ser Ala Met Gly Thr Asn Trp Val
            290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
            325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly Thr Ala Leu Pro
            355                 360                 365

Arg Val Gly Pro Val Arg Pro Thr Gly Gln Asp Trp Asn His Thr Pro
370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
            405                 410                 415

Ser Thr Leu Ser Ala Gln Pro Gln Leu Ser Arg Ser His Ser Ser Gly
            420                 425                 430

Ser Val Leu Pro Leu Gly Glu Leu Glu Gly Arg Arg Ser Thr Arg Asp
            435                 440                 445

Arg Arg Ser Pro Ala Glu Pro Glu Gly Gly Pro Ala Ser Glu Gly Ala
450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Phe Ser Pro Gln Leu Gln Glu Ser
            485                 490                 495

Val Phe His Leu Leu Val Pro Ser Val Ile Leu Val Leu Leu Ala Val
            500                 505                 510

Gly Gly Leu Leu Phe Tyr Arg Trp Arg Arg Arg Ser His Gln Glu Pro
            515                 520                 525

Gln Arg Ala Asp Ser Pro Leu Glu Gln Pro Glu Gly Ser Pro Leu Thr
530                 535                 540

Gln Asp Asp Arg Gln Val Glu Leu Pro Val
545                 550

<210> SEQ ID NO 18
<211> LENGTH: 242
<212> TYPE: PRT
<213> ORGANISM: Homo sapiens

<400> SEQUENCE: 18

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
            35                  40                  45

```
Ser Arg Leu Gln Tyr Met Lys His Tyr Phe Pro Ile Asn Tyr Lys Ile
 50                  55                  60

Ser Val Pro Tyr Glu Gly Val Phe Arg Ile Ala Asn Val Thr Arg Leu
 65                  70                  75                  80

Gln Arg Ala Gln Val Ser Glu Arg Glu Leu Arg Tyr Leu Trp Val Leu
                 85                  90                  95

Val Ser Leu Ser Ala Thr Glu Ser Val Gln Asp Val Leu Leu Glu Gly
                100                 105                 110

His Pro Ser Trp Lys Tyr Leu Gln Glu Val Glu Thr Leu Leu Leu Asn
            115                 120                 125

Val Gln Gln Gly Leu Thr Asp Val Glu Val Ser Pro Lys Val Glu Ser
    130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
                180                 185                 190

Val Pro Ser Pro Gln Ser Cys Ser Pro Glu Pro Ser Leu Gln Tyr Ala
            195                 200                 205

Ala Thr Gln Leu Tyr Pro Pro Pro Pro Trp Ser Pro Ser Ser Pro Pro
    210                 215                 220

His Ser Thr Gly Ser Val Arg Pro Val Arg Ala Gln Gly Glu Gly Leu
225                 230                 235                 240

Leu Pro
```

US 8,263,079 B2

ANTIBODIES AGAINST CSF-1R

This application claims the benefit of U.S. Provisional Application No. 61/319,896 which was filed 1 Apr. 2010.

This invention is directed to the fields of immunology and cancer treatment. More specifically, the present invention is directed to human antibodies that bind to human Colony Stimulating Factor-1 Receptor (CSF-1R).

Colony Stimulating Factor-1 Receptor (CSF-1R), also known as M-CSFR or CD-115, (Human CSF-1R variant; SEQ ID NO:15) (Human CSF-1R; SEQ ID NO:16; Uniprot Assession #P07333), encoded by the c-fms gene, is a tyrosine kinase receptor expressed selectively on macrophage and granulocyte cell lineages in normal individuals and on tumor cells in cancer. There are two known ligands, Colony Stimulating Factor-1 (CSF-1) (Human CSF-1; SEQ ID NO:17) (Uniprot Assession #P09603), also known as M-CSF, and IL-34 (Human IL-34; SEQ ID NO:18)(Uniprot Assession #Q6ZMJ4), that bind to the extracellular domain of CSF-1R. Upon CSF-1 or IL-34 binding, CSF-1R dimerizes, leading to trans-phosphorylation of the receptor and phosphorylation and activation of downstream signaling molecules such as MAPK and Akt. Phosphorylation of CSF-1R results in: (1) the proliferation and differentiation of macrophages from hematopoietic progenitor stem cells and (2) survival and migration of macrophages to various organs and tissues in the body, particularly the tumor stroma. CSF-1R can also be expressed on the surface of tumor cells.

Antibodies to murine CSF-1R are not cross-reactive in humans and consequently would be ineffective therapeutics for treating cancer in humans.

Human antibodies to CSF-1R are disclosed in PCT Publication WO2009/026303 (Brasel, et al.). Such antibodies do not induce Antibody-Dependent Cell-Mediated Cytotoxicity (ADCC) activity against cells bound by the antibodies. ADCC occurs when the antibody binds to a cell expressing the antigen (target cell), making the Fc region of the antibody available for binding to the Fc receptor on natural killer cells, monocytes, neutrophils and dendritic cells (effector cell). Antibodies disclosed in Brasel, are incapable of bringing the target cell and effector cell together to initiate the killing of the target cell.

Antibodies to the ligand are not cross reactive. Therefore antibodies to CSF-1 do not inhibit IL-34 binding to CSF-1R and antibodies to IL-34 do not inhibit CSF-1 binding to CSF-1R. Ligand binding to the receptor may have an effect on cancer growth. Additionally, antibodies to the ligand do not internalize, nor do they induce CSF-1R degradation, nor do they stimulate ADCC activity against cells.

A need exists for multifunctional antibodies which block the binding of ligands to CSF-1R and also induce ADCC activity against cells bound by the antibodies.

Antibodies of the present invention are advantageous over known antibodies because they have a multitude of functions. Antibodies of the invention block CSF-1 and IL-34 binding to the receptor, thereby preventing dimerization of the receptor and the resulting phosphorylation of the intracellular tyrosine residues, functions which are critical in preventing macrophage induced tumor growth. Antibodies of the invention internalize and induce CSF-1R degradation. Importantly, in addition to blocking ligand binding, antibodies of the invention enhance ADCC activity by stimulating the killing of tumor cells and tumor-associated macrophages and monocytes. Antibodies of the invention also simultaneously affect macrophage activity, an activity which plays a major role in tumor progression. Because of the multitude of therapeutic functions which they have, the antibodies of the present invention have a significant advantage over the antibodies known in the art.

SUMMARY OF THE INVENTION

One aspect of the present invention is an antibody, or fragment thereof, that specifically binds human CSF-1R variant (SEQ ID NO:15), comprising a CDRH1 comprising the sequence SYGMH (SEQ ID NO:1), a CDRH2 comprising the sequence VIWYDGSNKYYADSVKG (SEQ ID NO:2), a CDRH3 comprising the sequence GDYEVDYGMDV (SEQ ID NO:3), a CDRL1 comprising the sequence RASQGISNALA (SEQ ID NO:4), a CDRL2 comprising the sequence DASSLES (SEQ ID NO:5), and a CDRL3 comprising the sequence QQFNSYPWT (SEQ ID NO:6). Another aspect of the present invention is an antibody, or fragment thereof, that specifically binds human CSF-1R (SEQ ID NO:16), comprising a CDRH1 comprising the sequence SYGMH (SEQ ID NO:1), a CDRH2 comprising the sequence VIWYDGSNKYYADSVKG (SEQ ID NO:2), a CDRH3 comprising the sequence GDYEVDYGMDV (SEQ ID NO:3), a CDRL1 comprising the sequence RASQGISNALA (SEQ ID NO:4), a CDRL2 comprising the sequence DASSLES (SEQ ID NO:5), and a CDRL3 comprising the sequence QQFNSYPWT (SEQ ID NO:6). One aspect of the present invention is an antibody, or fragment thereof, that specifically binds human CSF-1R (SEQ ID NO:15), comprising a CDRH1 comprising the sequence SYGMH (SEQ ID NO:1), a CDRH2 comprising the sequence VIWYDGSNKYYADSVKG (SEQ ID NO:2), a CDRH3 comprising the sequence GDYEVDYGMDV (SEQ ID NO:3), a CDRL1 comprising the sequence RASQGISNALA (SEQ ID NO:4), a CDRL2 comprising the sequence DASSLES (SEQ ID NO:5), and a CDRL3 comprising the sequence QQFNSYPWT (SEQ ID NO:6). Antibodies of the present invention may further comprises an amino acid substitution within one of said CDR sequences. In another aspect, the aforementioned CDRs do not have an amino acid substitution in one of the CDR sequences.

Another aspect of the present invention is an antibody, or fragment thereof, that binds CSF-1R, and comprises a VH comprising the amino acid sequence:

```
                                              (SEQ ID NO: 7)
QDQLVESGGGVVQPGRSLRLSCAASGFTFSSYGMHWVRQAPGEGLEWV

AVIWYDGSNKYYADSVKGRFTISRDNSKNTLYLQMNSLRAEDTAVYYC

ARGDYEVDYGMDVWGQGTTVTVAS,
``` or a VL comprising the amino acid sequence:

```
                                              (SEQ ID NO: 8)
AIQLTQSPSSLSASVGDRVTITCRASQGISNALAWYQQKPGKAPKLLI

YDASSLESGVPSRFSGSGSGTDFTLTISSLQPEDFATYYCQQFNSYPW

TFGQGTKVEIK.
```

Another aspect of the present invention is an antibody, or fragment thereof, that binds CSF-1R, and comprises a light chain comprising the amino acid sequence of SEQ ID NO: 10 and a heavy chain comprising the amino acid sequence of SEQ ID NO: 9. In yet another aspect of the present invention, an antibody comprises two light chains each comprising the amino acid sequence of SEQ ID NO: 10 and two heavy chains each comprising the amino acid sequence of SEQ ID NO: 9.

CSF-1R-binding fragments of such antibodies are part of the invention.

The invention also provides isolated DNA and polynucleotides/polynucleic acids encoding the antibodies or fragments thereof described above, expression vectors comprising the polynucleotides, and host cells comprising the polynucleotides. The invention further provides methods of purifying the antibodies or fragments thereof. The invention further provides pharmaceutical compositions comprising the antibodies, or fragments thereof, polynucleotides, vectors or host cells of the present invention alone or with a pharmaceutically acceptable carrier, diluent or excipient. The invention provides pharmaceutical compositions comprising the antibodies, or fragments thereof, of the present invention together with a pharmaceutically acceptable carrier, diluent or excipient.

Additionally, the present invention is directed to methods of inhibiting growth of a cancer cell, and methods of treating leukemia, breast and prostate carcinomas, in mammals, by administering an effective amount of an antibody. Another aspect of the present invention is directed to methods of inhibiting growth of a cancer cell, and methods of treating leukemia, endometrial, breast and prostate carcinomas, in mammals, by administering an effective amount of an antibody. Yet another aspect of the present invention is directed to methods of inhibiting growth of a cancer cell, and methods of treating leukemia, endometrial, breast and prostate carcinomas, as well as ovarian cancer, colorectal cancer, hepatocellular cancer, renal cancer, multiple myeloma, and hodgkin's lymphoma. Antibodies of the present invention can be used to treat neoplastic diseases, including solid tumors, and for treatment of breast and prostate carcinomas. In another aspect, antibodies of the present invention can be used to treat neoplastic diseases, including solid tumors, and for treatment of breast, endometrial, and prostate carcinomas. In another aspect, antibodies of the present invention can be used to treat neoplastic diseases, including solid tumors, and for treatment of breast, endometrial, prostate, ovarian, colorectal, hepatocellular, and renal carcinomas.

One aspect of the present invention is the antibody, or fragments thereof, for use in therapy, or for use in treatment or for use as a medicament. In yet another aspect, the previously described antibodies or fragments thereof are for use in treating cancer. The present invention can be used in treating cancers that include but are not limited to leukemia, breast cancer and prostate cancer. In one aspect, the present invention can be used in treating cancers that include but are not limited to leukemia, breast cancer, endometrial cancer and prostate cancer. In another aspect, the present invention can be used in treating cancers that include but are not limited to leukemia, breast cancer, endometrial cancer, prostate cancer, ovarian cancer, colorectal cancer, hepatocellular cancer, renal cancer, multiple myeloma, and hodgkin's lymphoma.

The present invention also includes the antibody, or fragment thereof, of the present invention for use in treating cancer including providing or administering an effective amount of another anti-cancer treatment wherein the anti-cancer treatment includes but is not limited to an anti-angiogenesis agent, a chemotherapeutic agent, or an anti-neoplastic agent. Further, anti-neoplastic agents include but are not limited to docetaxel, paclitaxel, Herceptin® and doxorubicin. The anti-cancer treatment is administered to the patient in addition to the presently disclosed antibody or fragment. The antibody or fragment thereof is administered before, during, substantially simultaneously with, or after commencing therapy with other anti-cancer treatment or another anti-neoplastic agent.

The present invention also provides for use of an antibody of the invention for the manufacture of a medicament for the treatment of cancer. In a one aspect the cancer is leukemia, breast cancer, or prostate cancer. In a one aspect the cancer is leukemia, breast cancer, endometrial cancer, or prostate cancer. In another aspect of the present invention the cancer is leukemia, breast cancer, endometrial cancer, prostate cancer, ovarian cancer, colorectal cancer, hepatocellular cancer, renal cancer, multiple myeloma, or hodgkin's lymphoma. The use of the antibody includes providing or administering an effective amount of another anti-cancer treatment wherein the anti-cancer treatment includes but is not limited to an anti-angiogenesis agent, a chemotherapeutic agent, or an anti-neoplastic agent. Further, anti-neoplastic agents include but are not limited to docetaxel, paclitaxel, Herceptin® and doxorubicin. The anti-cancer treatment is administered to the patient in addition to the presently disclosed antibody or fragment. The antibody or fragment thereof is administered before, during, substantially simultaneously with, or after commencing therapy with other anti-cancer treatment or another anti-neoplastic agent.

The invention further provides for a method of treating cancer in a mammal, comprising administering to said mammal in need thereof an effective amount of the antibody or fragment thereof the present invention. The cancer is selected from the group consisting of leukemia, breast cancer, endometrial cancer, and prostate cancer. In another aspect, the cancer is selected from the group consisting of leukemia, breast cancer, endometrial cancer, prostate cancer, ovarian cancer, colorectal cancer, hepatocellular cancer, renal cancer, pancreatic cancer, multiple myeloma, and hodgkin's lymphoma. Additionally, the method can further comprise administering another anti-cancer treatment to said mammal The anti-cancer treatment is selected from the group consisting of an anti-angiogenesis agent, a chemotherapeutic agent, and an anti-neoplastic agent. The anti-neoplastic agent may be selected from the group consisting of docetaxel, paclitaxel, Herceptin® and doxorubicin.

The invention further provides methods of using the antibodies, or compositions, to treat a mammal in need thereof, for example, to inhibit angiogenesis or bone metastases, or to inhibit tumor or hyperproliferative growth or to treat inflammatory diseases. The invention further provides antibodies, or compositions, for use in treatment of a mammal in need thereof, for example, to inhibit angiogenesis or bone metastases, or inhibit tumor or hyperproliferative growth or inflammatory diseases.

The present invention is also directed to a product or pharmaceutical composition containing the presently disclosed antibody, or fragment thereof. In addition the product or pharmaceutical composition may also include an additional pharmaceutical agent, anti-neoplastic agent, or anti-cancer agent or treatment, including but not limited to docetaxel, paclitaxel, Herceptin® or doxorubicin, given in combination with the presently disclosed antibody simultaneous, separate or sequential in therapy.

The invention provides using CSF-1 levels in samples of blood, serum, plasma, tumor cells or circulating tumor cells as an indicator of the successful treatment with CSF-1R antibodies of the present invention, or fragments thereof, in patients if the cancer has CSF-1R expressed on the surface of tumor-associated macrophages. The invention also provides a method of treating cancer in a patient, comprising the steps: (1) measuring the level of CSF-1 in a sample taken from the patient wherein the sample is selected from the group consisting of blood, serum, plasma, tumor cells and circulating tumor cells, and (2) administering to the patient the antibody or fragment thereof of the present invention if the CSF-1 levels are higher than CSF-1 levels found in a control population.

The invention provides using IL-34 levels in samples of blood, serum, plasma, tumor cells or circulating tumor cells as an indicator of the successful treatment with CSF-1R antibodies of the present invention, or fragments thereof, in patients. The invention also provides a method of treating cancer in a patient, comprising the steps: (1) measuring the level of IL-34 in a sample taken from the patient wherein the sample is selected from the group consisting of blood, serum, plasma, tumor cells and circulating tumor cells, and (2) administering to the patient the antibody or fragment thereof of the present invention if the IL-34 levels are higher than IL-34 levels found in a control population.

One aspect of the present invention is a method for determining whether a subject having a cancer is a candidate for an anti-CSF-1R antibody-based cancer treatment regimen, wherein said antibody is the antibody of the present invention comprising: (1) ex vivo or in vitro determining the level of CSF-1 in a sample of the subject, wherein the sample is selected from the group consisting of blood, serum, plasma, tumor cells and circulating tumor cells; and (2) wherein an increase in the level of CSF-1, as compared with the level of CSF-1 in an individual not suffering from cancer, is indicative that the subject is a candidate for the anti-CSF-1R antibody-based cancer treatment regimen.

Another aspect of the present invention is a method for determining whether a subject having a cancer is a candidate for an anti-CSF-1R antibody-based cancer treatment regimen, wherein said antibody is the antibody of the present invention, comprising: (1) ex vivo or in vitro determining the level of IL-34 in a sample of the subject, wherein the sample is selected from the group consisting of blood, serum, plasma, tumor cells and circulating tumor cells; and (2) wherein an increase in the level of IL-34, as compared with the level of IL-34 in an individual not suffering from cancer, is indicative that the subject is a candidate for the anti-CSF-1R antibody-based cancer treatment regimen.

The invention also provides antibodies which bind specifically to CSF-1R. The antibodies have at least one property selected from (a) inhibit binding of CSF-1 or IL-34 to CSF-1R; (b) inhibit activation of CSF-1R; (c) reduce phosphorylation of CSF-1R; (d) reduce activation of MAPK; (e) reduce activation of Akt; (f) reduce CSF-1R amount; and (g) induce ADCC. A preferred embodiment of the present invention possesses properties (a) to (g).

One aspect of the present invention is an antibody, or fragment thereof, that specifically binds human CSF-1R variant (SEQ ID NO:15) or human CSF-1R (SEQ ID NO:16), and inhibits signaling of CSF-1R, internalizes and induces CSF-1R degradation, and stimulates Antibody-Dependent Cell-Mediated Cytotoxicity (ADCC) activity against a variety of cells including tumors, macrophages and monocytes. SEQ ID NO:15 and SEQ ID NO:16 differ by one amino acid at position 54 which falls outside the binding region.

As used herein, the term "antibody" includes immunoglobulin molecules comprising four polypeptide chains, two heavy (H) chains and two light (L) chains inter-connected by disulfide bonds. Individual chains can fold into domains having similar sizes (110-125 amino acids) and structures, but different functions.

The light chain can comprise one variable domain (abbreviated herein as VL) and/or one constant domain (abbreviated herein as CL). The light chains of human antibodies (immunoglobulins) are either kappa (K) light chains or lambda (2) light chains. The expression VL, as used herein, is intended to include both the variable regions from kappa-type light chains (VK) and from lambda-type light chains (Vλ). The heavy chain can also comprise one variable domain (abbreviated herein as VH) and/or, depending on the class or isotype of antibody, three or four constant domains (CH1 CH2, CH3 and CH4) (abbreviated herein collectively as CH). In humans, the isotypes are IgA, IgD, IgE, IgG, and IgM, with IgA and IgG further subdivided into subclasses or subtypes (IgA1-2 and IgG1-4). The present invention includes antibodies of any of the aforementioned classes or subclasses. Human IgG$_1$ is the preferred isotype for the antibodies of the present invention.

Three regions, called hypervariable or complementarity-determining regions (CDRs), are found in each of VL and VH, which are supported by less variable regions called frameworks (abbreviated herein as FR). Amino acids are assigned to a particular CDR region or domain in accordance with Kabat convention (Kabat, et al., Ann. NY Acad. Sci. 190:382-93 (1971); Kabat, et al., Sequences of Proteins of Immunological Interest, Fifth Edition, U.S. Department of Health and Human Services, NIH Publication No. 91-3242 (1991).). Each VH and VL is composed of three CDRs and four FRs, arranged from amino-terminus to carboxy-terminus in the following order: FR1-CDR1-FR2-CDR2-FR3-CDR3-FR4. The portion of an antibody consisting of VL and VH domains is designated Fv (Fragment variable) and constitutes the antigen-binding site. Single chain Fv (scFv) is an antibody fragment containing a VL domain and a VH domain on one polypeptide chain, wherein the N terminus of one domain and the C terminus of the other domain are joined by a flexible linker.

An "isolated antibody" is an antibody that (1) has been partially, substantially, or fully purified from a mixture of components; (2) has been identified and separated and/or recovered from a component of its natural environment; (3) is monoclonal; (4) is free of other proteins from the same species; (5) is expressed by a cell from a different species; or (6) does not occur in nature. Components, as used herein, exclude the antibody of the present invention. Contaminant components of its natural environment are materials which would interfere with diagnostic or therapeutic uses for the antibody, and may include enzymes, hormones, and other proteinaceous or non-proteinaceous solutes. Examples of isolated antibodies include an antibody that has been affinity purified, an antibody that has been made by a hybridoma or other cell line in vitro, and a human antibody derived from a transgenic mouse.

The term "monoclonal antibody," as used herein, refers to an antibody obtained from a population of substantially homogeneous antibodies, e.g., the individual antibodies comprising the population are substantially identical except for possible naturally occurring mutations or minor post-translational variations that may be present. Monoclonal antibodies are highly specific, being directed against a single antigenic site (also known as determinant or epitope). Furthermore, in contrast to conventional (polyclonal) antibody preparations which typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

The term "human antibody," as used herein, includes antibodies having variable and constant regions corresponding to human germline immunoglobulin sequences (as described in Kabat et al., supra). The human antibodies of the invention may include amino acid residues not encoded by human germline immunoglobulin sequences (e.g., mutations introduced by random or site-specific mutagenesis in vitro or by somatic mutation in vivo), for example in the CDRs. The human antibody can have at least one position replaced with an amino acid residue, e.g., an activity enhancing amino acid residue which is not encoded by the human germline immunoglobulin sequence. However, the term "human antibody", as used herein, is not intended to include antibodies in which CDR sequences derived from the germline of another mammalian species, such as a mouse, have been grafted onto human framework sequences. Methods of producing a "human antibody", as used herein are not intended to include antibodies produced in a human being.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal that is transgenic for human immunoglobulin genes, or antibodies prepared, expressed, created or isolated by any other means that involves splicing of human immunoglobulin gene sequences to other DNA sequences. Such recombinant human antibodies have variable and constant regions derived from human germline immunoglobulin sequences.

Fc (Fragment, crystallizable region) is the designation for the portion or fragment of an antibody that consists of paired heavy chain constant domains. In an IgG antibody, for example, the Fc consists of heavy chain CH2 and CH3 domains. The Fc of an IgA or an IgM antibody further comprises a CH4 domain. The Fc is associated with Fc receptor binding, activation of antibody-dependent cell-mediated cytotoxicity (ADCC) and/or cell mediated cytotoxicity (CMC). For antibodies such as IgA and IgM, which are complexes of multiple IgG like proteins, complex formation requires Fc constant domains.

Thus, antibodies of the invention include, but are not limited to, isolated antibodies, human antibodies, humanized antibodies, recombinant human antibodies, monoclonal antibodies, digestion fragments, specified portions and variants thereof, including antibody mimetics or comprising portions of antibodies that mimic the structure and/or function of an antibody or specified fragment or portion thereof; each containing at least one CDR. Functional fragments include antigen binding fragments that bind to a CSF-1R antigen. For example, antibody fragments capable of binding to CSF-1R, or a portion thereof, and which are embraced by the present invention include bivalent fragments such as (Fab')$_2$ with inter-chain disulfide bonds intact, monovalent fragments such as Fab (Fragment, antigen binding) which refers to the fragments of the antibody consisting of VL-CL and VH-CH1 domains and do not retain the heavy chain hinge region (e.g., by papain digestion), Fabs which retain the heavy chain hinge region, Facb (e.g., by plasmin digestion), F(ab')$_2$, Fab' which lack disulfide bonds, pFc' (e.g., by pepsin or plasmin digestion), Fd (e.g., by pepsin digestion, partial reduction and re-aggregation) and Fv or scFv (e.g., by molecular biology techniques). Antibody fragments are also intended to include, e.g., domain deleted antibodies, linear antibodies, single chain antibodies, scFv, single domain antibodies, multivalent single chain antibodies, multi-specific antibodies formed from antibody fragments including diabodies, triabodies, and the like that bind specifically with antigens.

The hinge region separates the Fab and Fc portions of the antibody, providing for mobility of Fabs relative to each other and relative to Fc, as well as including multiple disulfide bonds for covalent linkage of the two heavy chains.

Antibody formats have been developed which retain binding specificity, but have other characteristics that may be desirable, including for example, bispecificity, multivalence (more than two binding sites), and compact size (e.g., binding domains alone). The antibodies of the present invention are specific for CSF-1R. Antibody specificity refers to selective recognition of the antibody for a particular epitope of an antigen. Antibodies of the present invention, for example, can be monospecific or bispecific. Bispecific antibodies (BsAbs) are antibodies that have two different antigen-binding specificities or sites. Where an antibody has more than one specificity, the recognized epitopes can be associated with a single antigen or with more than one antigen. Thus, the present invention provides bispecific antibodies that bind to two different antigens, with at least one specificity for CSF-1R. As stated above, such antibodies include any fragments thereof.

Specificity of the present antibodies or fragments thereof, for CSF-1R can be determined based on affinity and/or avidity. Affinity, represented by the equilibrium constant for the dissociation of an antigen with an antibody ($K_D$), measures the binding strength between an antigenic determinant and an antibody-binding site.

The antibodies, or fragments thereof, of the invention bind to an epitope of CSF-1R located on the extracellular domain segments (hereinafter referred simply to as "domains" or "ECD"). The term "epitope" as used herein refers to discrete, three-dimensional sites on an antigen that are recognized by the antibodies of the invention. Epitopes are the immunologically active regions on a complex antigen, the regions that actually bind to a B-cell receptor, and that are actually bound by the resulting antibody molecules that are produced by the B cell. Antigens generally contain at least one epitope and usually more than one epitope. Epitopes on protein antigens can be linear or non-linear. Linear epitopes are those comprised of contiguous amino acid residues in the amino acid sequence of a protein. Linear epitopes may or may not require conformational folding to form the native three-dimensional structure and elicit an immune response that produces antibodies with binding specificity to the antigen. Non-linear epitopes are comprised of non-contiguous amino acid residues. Thus, non-linear epitopes always require some degree of protein folding to bring the requisite amino acid residues into the proximity of one another to form the native three-dimensional structure and elicit an immune response that produces antibodies with binding specificity to the antigen.

Antibodies of the present invention also include those for which binding characteristics have been improved by direct mutation, methods of affinity maturation, phage display, or chain shuffling. Affinity and specificity can be modified or improved by mutating CDR and/or FW residues and screening for antigen binding sites having the desired characteristics (see e.g., Yang et al., J. Mol. Biol., 254: 392-403 (1995)). CDRs are mutated in a variety of ways. One way is to randomize individual residues, or combinations of residues, so that in a population of, otherwise identical antigen binding sites, subsets of from two to twenty amino acids are found at particular positions. Alternatively, mutations can be induced over a range of residues by error prone PCR methods (see e.g., Hawkins et al., J. Mol. Biol., 226: 889-96 (1992)). In another example, phage display vectors containing heavy and light chain variable region genes can be propagated in mutator strains of *E. coli* (see e.g., Low et al., J. Mol. Biol., 250: 359-68 (1996)). These methods of mutagenesis are illustrative of the many methods known to one of skill in the art.

A convenient way for generating substitutional variants is affinity maturation using phage display. Briefly, several CDR region sites are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity ($K_D$), specificity, EC50) as herein disclosed. In order to identify candidate CDR region sites for modification, alanine scanning mutagenesis can be performed to identify CDR region residues contributing significantly to antigen binding. Alternatively, or in addition, random mutagenesis may be performed on one or more CDR sequences at one or more residue positions, either while the CDR is operably linked to the variable region or while the CDR is independent of other variable region sequence and then the altered CDR returned to a variable region using recombinant DNA technology. Once such variant antibodies are generated and expressed, the panel of variants is subjected to screening as described herein, and antibodies with superior properties in one or more relevant assays may be selected for further development.

In addition to the antibodies specifically described herein, other "substantially homologous" modified antibodies can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis.

The present invention includes nucleic acid sequences that encode an anti-CSF-1R antibody heavy chain, comprising any one of the VH regions or a portion thereof, or any one of the VH CDRs, including any variants thereof, as disclosed herein. The invention also includes nucleic acid molecules that encode an anti-CSF-1R antibody light chain comprising any one of the VL regions, or a portion thereof or any one of the VL CDRs, including any variants thereof as disclosed herein. The invention also includes the nucleic acid sequences of Antibody 1, SEQ ID NOs 13 and 14 for heavy chain and light chain respectively. The antibodies of the invention include antibodies comprising the same CDR regions of Antibody 1, and/or the same light chain variable region and/or heavy chain variable region of Antibody 1.

The antibodies of the present invention may be produced by methods known in the art. These methods include the immunological method described by Kohler and Milstein, Nature 256: 495-497 (1975); Laboratory Techniques in Biochemistry and Molecular Biology, Volume 13 (Burdon et al. eds., Elsevier Science Publishers, Amsterdam) in Monoclonal Antibody Technology, The Production and Characterization of Rodent and Human Hybridomas (Campbell ed., 1984); as well as by the recombinant DNA method described by Huse et al., Science 246: 1275-1281 (1989). The antibodies can also be obtained from libraries bearing combinations of VH and VL domains in the form of scFv or Fab. The VH and VL domains can be encoded by nucleotides that are synthetic, partially synthetic, or naturally derived. The present invention can be made by phage display libraries bearing human antibody fragments. Other sources of human antibodies are transgenic mice engineered to express human immunoglobulin genes.

One embodiment for the preparation of antibodies is the expression of the nucleic acid encoding the antibody according to the invention in a transgenic animal that has a substantial portion of the human antibody producing genome inserted and is rendered deficient in the production of endogenous antibodies. Transgenic animals include but are not limited to mice, goat, and rabbit. The antibodies of the present invention were made with transgenic mice. One further embodiment of the invention includes expression of the antibody-coding gene in, for example, the mammary gland of the animal for secretion of the polypeptide during lactation.

A common method for producing "humanized" antibodies is to graft CDR sequences from a MAb (produced by immunizing a rodent host) onto a human Ig backbone, and transfection of the chimeric genes into Chinese Hamster Ovary (CHO) cells which in turn produce a functional antibody that is secreted by the CHO cells.

It is understood that amino acid residues that are primary determinants of binding of single domain antibodies can be within Kabat or Chothia defined CDRs, but may include other residues as well, such as, for example, residues that would otherwise be buried in the VH-VL interface of a VH-VL heterodimer.

The protein used to identify CSF-1R binding antibodies of the invention is preferably CSF-1R and, more preferably, is the extracellular domain of CSF-1R. The CSF-1R extracellular domain can be free or conjugated to another molecule. The antibodies of this invention can be fused to additional amino acid residues. Such amino acid residues can be a peptide tag, perhaps to facilitate isolation or an IgG FC portion to optimize dimerization. Other amino acid residues for homing of the antibodies to specific organs or tissues are also contemplated.

Antibody fragments can be produced by cleaving a whole antibody, or by expressing DNA that encodes the fragment. Fragments of antibodies may be prepared by methods described by Lamoyi et al., J. Immunol. Methods 56: 235-243 (1983) and by Parham, J. Immunol. 131: 2895-2902 (1983). Such fragments may contain one or both Fab fragments or the F(ab')$_2$ fragment. Such fragments may also contain single-chain fragment variable region antibodies, i.e. scFv, diabodies, or other antibody fragments. Methods of producing such functional equivalents are disclosed in: European Patent Application Publication No. EP 239,400 (Winter); PCT Publication WO 89/09622 (Hann, et al.); European Patent Application Publication No. EP 338,745 (Owens, et al.); and European Patent Application Publication No. EP 332,424 (Beldler, et al.). Throughout this specification, the term "antibodies" of the invention includes any fragments thereof, whether or not specifically stated.

Preferred host cells for transformation of vectors and expression of the antibodies of the present invention are mammalian cells, e.g., NS0 cells (non-secreting (0) mouse myeloma cells), 293, SP20 and CHO cells and other cell lines of lymphoid origin such as lymphoma, myeloma, or hybridoma cells. Other eukaryotic hosts, such as yeasts, can be alternatively used.

The antibodies of the present invention may be isolated or purified by any method known in the art, including precipitation by ammonium sulfate or sodium sulfate followed by dialysis against saline, ion exchange chromatography, affinity or immuno-affinity chromatography, as well as gel filtration or zone electrophoresis. A preferred method of purification for the antibodies of the current invention is Protein-A affinity chromatography.

DNA encoding human antibodies can be prepared by recombining DNA encoding human constant regions and variable regions, other than the CDRs, derived substantially or exclusively from the corresponding human antibody regions and DNA encoding CDRs derived from a human.

Suitable sources of DNA that encode fragments of antibodies include any cell, such as hybridomas and spleen cells that express the full-length antibody. The fragments may be used by themselves as antibody equivalents, or may be recombined into equivalents, as described above. The DNA recombination and other techniques described herein may be carried out by known methods. Another source of DNA is a phage display library of antibodies, as is known in the art.

Additionally, the present invention provides expression vectors containing the polynucleotide sequences previously described operably linked to a control sequence such as an expression sequence, a promoter and/or an enhancer sequence. A variety of expression vectors for the efficient synthesis of antibody polypeptide in prokaryotic systems, such as bacteria and eukaryotic systems, including but not limited to, yeast and mammalian cell culture systems have been developed. The vectors of the present invention can comprise segments of chromosomal, non-chromosomal and synthetic DNA sequences.

Any suitable expression vector can be used. For example, prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages. An example of a vector useful in yeast is the 2μ plasmid. Suitable vectors for expression in mammalian cells include well-known derivatives of SV-40, CMV, adenovirus, retrovirus-derived DNA sequences, and shuttle vectors derived from combination of functional mammalian vectors, such as those described above, and functional plasmids and phage DNA. Additional eukaryotic expression vectors are known in the art (e.g., P. J. Southern and P. Berg, J. Mol. Appl. Genet. 1: 327-41 (1982); Subramani et al., Mol. Cell. Biol. 1: 854-64 (1981); Kaufmann and Sharp, J. Mol. Biol. 159: 601-21 (1982); Scahill et al., Proc. Nat'l Acad. Sci. USA 80: 4654-59 (1983); Urlaub and Chasin, Proc. Nat'l Acad. Sci. USA 77: 4216-20) (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., PhoS, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Where it is desired to express a gene construct in yeast, a suitable selection gene for use in yeast is the trp1 gene present in the yeast plasmid YRp7. The trp1 gene provides a selection marker for a mutant strain of yeast lacking the ability to grow in tryptophan, for example, ATCC No. 44076. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

The present invention also provides recombinant host cells containing the recombinant vectors previously described. Antibodies of the present invention can be expressed in cell lines other than in hybridomas. Nucleic acids, which comprise a sequence encoding a polypeptide according to the invention, can be used for transformation of a suitable mammalian host cell.

Cell lines of particular preference are selected based on high levels of expression, constitutive expression of protein of interest and minimal contamination from host proteins. Mammalian cell lines available as hosts for expression are well known in the art and include many immortalized cell lines, such as but not limited to, COS-7 cells, Chinese Hamster Ovary (CHO) cells, Baby Hamster Kidney (BHK) cells and many others including cell lines of lymphoid origin such as lymphoma, myeloma, or hybridoma cells. Suitable additional eukaryotic cells include yeast and other fungi. Useful prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, *Pseudomonas*, *Bacillus*, such as *Bacillus subtilis*, and *Streptomyces*.

These recombinant host cells can be used to produce an antibody, or fragment thereof, by culturing the cells under conditions permitting expression of the antibody or fragment thereof and purifying the antibody or fragment thereof from the host cell or medium surrounding the host cell. Targeting of the expressed antibody or fragment for secretion in the recombinant host cells can be facilitated by inserting a signal or secretory leader peptide-encoding sequence at the 5' end of the antibody-encoding gene of interest. These secretory leader peptide elements can be derived from either prokaryotic or eukaryotic sequences. Accordingly, suitable secretory leader peptides are used, being amino acids joined to the N-terminal end of a polypeptide to direct movement of the polypeptide out of the host cell cytosol and secretion into the medium.

The transformed host cells are cultured by methods known in the art in a liquid medium containing assimilable sources of carbon (carbohydrates such as glucose or lactose), nitrogen (amino acids, peptides, proteins or their degradation products such as peptones, ammonium salts or the like), and inorganic salts (sulfates, phosphates and/or carbonates of sodium, potassium, magnesium and calcium). The medium furthermore contains, for example, growth-promoting substances, such as trace elements, for example iron, zinc, manganese and the like.

A method of treating tumor growth in a mammal by administering to the mammal an effective amount of an antibody is also provided by the present invention. Suitable conditions to be treated according to the present invention involve cells preferably expressing CSF-1R. While not intended to be bound to any particular mechanism, the present methods provide for treatment of the growth of cancer cells including for example, those in which neoplastic growth, bone metastases, organ transplant rejection or an immune disorder such as an autoimmune disease which is stimulated by CSF-1R.

"Treatment" or "treat", in the context of the present invention refers to therapeutic treatment including inhibiting, slowing, lessening or reversing the progress of the underlying condition or undesired physiological change associated with a disease or disorder, ameliorating clinical symptoms of a condition or preventing the appearance of clinical symptoms of the condition. Beneficial or desired clinical results include, but are not limited to, alleviation of symptoms, diminishment of the extent of a disease or disorder, stabilization of a disease or disorder (i.e., where the disease or disorder does not worsen), delay or slowing of the progression of a disease or disorder, amelioration or palliation of the disease or disorder, and remission (whether partial or total) of the disease or disorder, whether detectable or undetectable. Treatment can also mean prolonging survival as compared to expected survival if not receiving treatment. Those in need of treatment include those already with the disease. In one embodiment, the present invention can be used as a medicament.

In the methods of the present invention, a therapeutically effective amount of an antibody of the invention is administered to a mammal or patient in need thereof. Additionally, the pharmaceutical compositions of the invention may include a therapeutically effective amount of an anti-CSF-1R antibody of the invention. A "therapeutically effective amount" or "effective dose" refers to an amount effective, at dosages and for periods of time necessary, to achieve the desired therapeutic result. A therapeutically effective amount of the antibody may vary according to factors such as the disease state, age, sex, and weight of the individual, and the ability of the antibody or antibody portion to elicit a desired response in the individual. Other factors include administration, target site, physiological state of the patient, whether the patient is human or an animal, other medications administered, and whether treatment is prophylactic or therapeutic. Although human antibodies of the invention are particularly useful for administration to humans, they can be administered to other mammals as well. The term mammal as used herein is intended to include, but is not limited to, humans, laboratory animals, domestic pets and farm animals. A therapeutically effective amount is also one in which any toxic or detrimental effects of the antibody or antibody portion are outweighed by the therapeutically beneficial effects.

Dosage regimens may be adjusted to provide the optimum desired response (e.g., a therapeutic or prophylactic response). Treatment dosages may be titrated using routine methods known to those of skill in the art to optimize safety and efficacy. Dosing schedules will typically range from a single bolus dosage or continuous infusion to multiple administrations per day (e.g., every 4-6 hours), or as indicated by the treating physician and the patient's condition. An exemplary, non-limiting range for a therapeutically effective amount of an antibody of the invention is 0.1-50 mg/kg, more preferably 3-35 mg/kg, and more preferably 5-20 mg/kg. Dosing amounts and frequencies will be determined by the physicians treating the patient and may include doses from less than 1 mg/kg to over 100 mg/kg given daily, three times per week, weekly, once every two weeks, or less often. It should be noted, however, that the present invention is not limited to any particular dose.

Anti-CSF-1R antibodies can be administered in combination with one or more other anti-cancer treatments including but not limited to an anti-angiogenesis agent, a chemotherapeutic agent, and an anti-neoplastic agent. Any suitable anti-cancer agent can be used, such as a chemotherapeutic agent, radiation, antibody or combinations thereof.

Anti-cancer agents include but are not limited to anti-neoplastic agents, antibodies, adjuvants, and prodrugs. The anti-neoplastic agents which are presently known in the art, or being evaluated, can be grouped into a variety of classes including, for example, mitotic inhibitors, alkylating agents, anti-metabolites, intercalating antibiotics, growth factor inhibitors, cell cycle inhibitors, enzymes, topoisomerase inhibitors, anti survival agents, biological response modifiers, anti-hormones, and anti-angiogenesis agents. Examples of alkylating agents include, but are not limited to, cisplatin, cyclophosphamide, melphalan, and dacarbazine. Examples of anti-metabolites include, but are not limited to, doxorubicin, daunorubicin, paclitaxel, gemcitabine, ALIMTA® and topoisomerase inhibitors irinotecan (CPT-11), aminocamptothecin, camptothecin, DX-8951f, topotecan (topoisomerase I), etoposide (VP-16), and teniposide (VM-26) (topoisomerase II). When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity tumor being treated, and the route of administration of the agent. It should be emphasized, however, that the present invention is not limited to any particular dose. In one aspect, docetaxel is a preferred anti-neoplastic agent of the invention. In other aspects of the invention paclitaxel, Herceptin® and doxorubicin are the preferred anti-neoplastic agents.

Anti-CSF-1R antibodies of the invention can be administered with antibodies that neutralize other receptors involved in tumor growth or angiogenesis. In an embodiment of the invention, an anti-CSF-1R antibody is used in combination with a receptor antagonist that binds specifically to Her2. Another example of such a receptor is VEGFR. An anti-CSF-1R antibody can be used in combination with a VEGFR antagonist. A CSF-1R antibody can also be administered in combination with one or more suitable adjuvants, such as, for example, cytokines (IL-10, IL-4 and IL-13, for example) or other immune stimulators, such as, but not limited to, chemokine, tumor-associated antigens, and peptides.

In the present invention, any suitable method or route can be used to administer anti-CSF-1R antibodies of the invention, and optionally, to co-administer anti-neoplastic agents and/or antagonists of other receptors. In a combination therapy of the present invention, the anti-CSF-1R antibody can be administered before, during, substantially simultaneous with, or after commencing therapy with another agent, including but not limited to docetaxel, paclitaxel, Herceptin® or doxorubicin, as well as any combination thereof. The anti-neoplastic agent regimens utilized according to the invention, include any regimen believed to be optimally suitable for the treatment of the patient's neoplastic condition. Different malignancies can require use of specific anti-tumor antibodies and specific anti-neoplastic agents, which will be determined on a patient to patient basis. Routes of administration include, for example, oral, intravenous, intraperitoneal, subcutaneous, or intramuscular administration. The dose of antagonist administered depends on numerous factors, including, for example, the type of antagonists, the type and severity tumor being treated and the route of administration of the antagonists. It should be emphasized, however, that the present invention is not limited to any particular method or route of administration.

The anti-CSF-1R antibodies of the invention, where used in a mammal for the purpose of prophylaxis or treatment, are preferably formulated as pharmaceutical compositions. Such pharmaceutical compositions and processes for preparing the same are well known in the art. See, e.g. Remington: The Science and Practice of Pharmacy (Gennaro A., et al., eds., 19th ed., Mack Publishing Co., 1995).

In another aspect of the invention, antibodies of the invention can be administered in conjunction with, or chemically or biosynthetically linked to, anti-cancer agents, anti-neoplastic or anti-angiogenic agents or detectable signal-producing agents. Anti-tumor agents linked to an antibody include any agents which destroy or damage neovasculature or a tumor or macrophages to which the antibody has bound or in the environment of the cell to which the antibody has bound. The present invention may be an anti-CSF-1R antibody administered as a conjugate, including but not limited to an immunoconjugate, which binds specifically to the receptor and delivers a toxin following ligand-toxin internalization. The antibody-agent conjugate can be directly linked to each other or via a linker, peptide or non-peptide. For example, an anti-tumor agent or anti-macrophage agent is a toxic agent such as an anti-neoplastic agents or a radioisotope. Suitable anti-neoplastic agents, including chemotherapeutic agents, are known to those skilled in the art and are discussed infra. The invention further contemplates anti-CSF-1R antibodies linked to target or reporter moieties, including by way of example only anti-neoplastic agents, other antibodies or reporters, such as radiolabled isotopes, in a diagnostic system where a detectable signal-producing agent is conjugated to the antibody.

In accordance with the invention, a method of inhibiting angiogenesis comprises administering a composition containing an antibody or antibody fragment of the invention to a mammal for a time and in an amount effective to inhibit angiogenesis. Similarly, the antibodies and antibody fragments can be used in methods of inhibiting tumor metastasis in a mammal by administering a composition containing an antibody of the invention to a mammal for a time and in an amount effective to inhibit metastasis of a tumor.

In accordance with the invention, a method of inhibiting macrophage infiltration into the tumor stroma and stimulating tumor growth comprises administering a composition containing an antibody or antibody fragment of the invention to a mammal for a time and in an amount effective to inhibit the effects of macrophages on tumor growth. Similarly, the antibodies and antibody fragments can be used in methods of alleviating bone erosion around a tumor metastasis in a mammal by administering a composition containing an antibody of the invention to a mammal for a time and in an amount effective to inhibit bone erosion.

The invention contemplates using the CSF-1R ligand (CSF-1 or IL-34) as a biomarker in the blood, serum, plasma, tumor cells or circulating tumor cells, of cancer patients who respond to treatment when the cancer has CSF-1R expressed on the surface of tumor-associated macrophages. The invention further contemplates the method of predicting successful treatment of a patient with the antibody or fragment of the present invention by measuring the CSF-1 levels in blood in a sample wherein the sample is selected from the group consisting of serum, plasma, tumor cells or circulating tumor cells. Another aspect of the invention is a method of treating cancer in a patient, comprising the steps: (1) measuring the level of CSF-1 in a sample taken from the patient wherein the sample is selected from the group consisting of blood, serum, plasma, tumor cells and circulating tumor cells, and (2) administering to the patient the antibody, or fragment thereof, of the present invention if the CSF-1 levels are higher than CSF-1 levels found in a control population. The invention further contemplates the method of predicting successful treatment of a patient with the antibody or fragment of the present invention by measuring the IL-34 levels in blood in a sample wherein the sample is selected from the group consisting of serum, plasma, tumor cells or circulating tumor cells. Another aspect of the invention is a method of treating cancer in a patient, comprising the steps: (1) measuring the level of IL-34 in a sample taken from the patient wherein the sample is selected from the group consisting of blood, serum, plasma, tumor cells and circulating tumor cells, and (2) administering to the patient the antibody, or fragment thereof, of the present invention if the IL-34 levels are higher than IL-34 levels found in a control population.

The present invention also contemplates a method for determining whether a subject having a cancer is a candidate for an anti-CSF-1R antibody-based cancer treatment regimen, wherein said antibody is the antibody of the present invention comprising: (1) ex vivo or in vitro determining the level of CSF-1 in a sample of the subject, wherein the sample is selected from the group consisting of blood, serum, plasma, tumor cells and circulating tumor cells; and (2) wherein an increase in the level of CSF-1, as compared with the level of CSF-1 in an individual not suffering from cancer, is indicative that the subject is a candidate for the anti-CSF-1R antibody-based cancer treatment regimen.

The present invention further contemplates a method for determining whether a subject having a cancer is a candidate for an anti-CSF-1R antibody-based cancer treatment regimen, wherein said antibody is the antibody of the present invention, comprising: (1) ex vivo or in vitro determining the level of IL-34 in a sample of the subject, wherein the sample is selected from the group consisting of blood, serum, plasma, tumor cells and circulating tumor cells; and (2) wherein an increase in the level of IL-34, as compared with the level of IL-34 in an individual not suffering from cancer, is indicative that the subject is a candidate for the anti-CSF-1R antibody-based cancer treatment regimen.

The present invention also contemplates a method for determining whether a subject having a cancer is a candidate for an anti-CSF-1R antibody-based cancer treatment regimen, wherein said antibody is the antibody of the present invention comprising: (1) ex vivo or in vitro determining the level of CSF-1, or IL-34, or both, in a sample of the subject, wherein the sample is selected from the group consisting of blood, serum, plasma, tumor cells and circulating tumor cells; and (2) wherein an increase in the level of CSF-1, or IL-34, or both, as compared with the level of CSF-1, or IL-34, or both, in an individual not suffering from cancer, is indicative that the subject is a candidate for the anti-CSF-1R antibody-based cancer treatment regimen.

CSF-1 or IL-34 levels can be measured in a variety of methods including commercially available kits (R&D Systems for CSF-1 and USCN Life Sciences, Inc. for IL-34). In one such technique, either CSF-1 or IL-34 standards or samples are added to a plate pre-coated with antibodies to human CSF-1 or IL-34 to allow binding of CSF-1 or IL-34 to the antibodies. After washing unbound CSF-1 or IL-34 and other proteins, a secondary antibody is added that recognizes the anti-CSF-1 or IL-34 antibody, respectively. The secondary antibody is coupled to horseradish peroxidase that emits a bluish color when substrate is added to the wells. The intensity of the color correlates to the quantity of CSF-1 or IL-34 found in the plate.

Since CSF-1 and IL-34 are naturally occurring in a healthy human body, a CSF-1 and a IL-34 baseline would need to be determined in a control population. The control population may include a group of individuals that have not been diagnosed as having a cancerous condition or signs of infection. Accordingly, the control population will establish a range of CSF-1 and IL-34 levels which are normal or baseline for healthy individuals. For example, CSF-1 levels are 68% or 77% higher in breast or colorectal cancer patient sera, respectively, than in sera of control groups (Lawicki et al., Clin. Chim. Acta 317: 112-116 (2006); Mroczho et al., Clin. Chim. Acta 380: 208-212 (2007)). In one aspect of the invention, CSF-1R ligand levels are at least 50% higher in cancer patient samples than in samples from the control population. The range of CSF-1 and/or IL-34 levels in the control population will be compared to the CSF-1 and/or IL-34 level identified from the patient's sample or samples to determine if the patient's CSF-1 and/or IL-34 level is higher than the baseline range of the control population.

In one aspect, the antibodies of the present invention are for use in treating cancer wherein the cancer cells are ligand secreting. In another aspect, the antibodies of the present invention are for use in treating cancer wherein the cancer cells are CSF-1 secreting. In yet another aspect, the antibodies of the present invention are for use in treating cancer wherein the cancer cells are IL-34 secreting.

The present invention also includes kits for inhibiting tumor growth and/or angiogenesis comprising a therapeutically effective amount of a human anti-CSF-1R antibody. The kits can further comprise the antibody or fragment thereof and an additional agent inducing additional anti-cancer agents, anti-neoplastic agents or treatments, including but not limited to docetaxel, paclitaxel, Herceptin® or doxorubicin. Alternatively, or in addition to, the kits can contain any suitable antagonist of, for example, another growth factor receptor involved in tumorigenesis or angiogenesis discussed infra. The kits of the present invention can further comprise an adjuvant.

Accordingly, the present receptor antibodies thus can be used in vivo and in vitro for investigative, diagnostic, prophylactic, or treatment methods, which are well known in the art. Variations in the principles of invention herein disclosed can be made by one skilled in the art and it is intended that such modifications are to be included within the scope of the present invention.

It is to be understood and expected that variations in the principles of invention herein disclosed can be made by one skilled in the art and it is intended that such modifications are to be included within the scope of the present invention.

EXAMPLES

The following examples further illustrate the invention, but should not be construed to limit the scope of the invention in any way; they should in no way be construed as limiting the broad scope of the invention. Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J. et al., Molecular Cloning: A Laboratory Manual, 2nd ed., Cold Spring Harbor Laboratory Press (1989) and Coligan, J. et al. Current Protocols in Immunology, Wiley & Sons, Incorporated (2007).

Expression and Purification of Human Anti-CSF-1R Antibodies

For each antibody, engineer a suitable heavy chain nucleotide sequence, for example SEQ ID NO. 13 for Antibody 1 into a suitable expression plasmid, for example pGSHC, and engineer a suitable light chain nucleotide sequence, for example SEQ ID NO. 14 for Antibody 1 into a suitable expression plasmid, such as pGSLC, by a suitable method such as PCR cloning. To establish a stable cell line, cotransfect in a suitable host cell line, such as NSO or CHO cells, with linearized heavy and light chain plasmids by electroporation and culture in suitable media such as glutamine free Dulbecco's Modified Eagle Medium with dialyzed fetal calf serum and glutamine synthetase supplement. Screen clones for antibody expression by an enzyme-linked immunosorbent assay (ELISA) and select the highest producer for culture in spinner flasks. Purify antibodies by a suitable method such as protein-A affinity chromatography.

Table 1 provides the amino acid sequences and SEQ ID NOs. of the various CDRs of Antibody 1 of present invention.

All CDR sequences are determined using the Kabat convention. Table 2 provides the SEQ ID NOs. of the various sequences related to the present invention. Polynucleic acid sequences that encode the amino acid sequences disclosed below are also included within the scope of the present invention.

TABLE 1

Amino Acid Sequence of Antibody 1
Heavy and Light Chain Variable Region CDRs

|  | Heavy Chain | SEQ ID NO. | Light Chain | SEQ NO ID. |
|---|---|---|---|---|
| CDR1 | SYGMH | 1 | RASQGISNALA | 4 |
| CDR2 | VIWYDGSNKYYADSVKG | 2 | DASSLES | 5 |
| CDR3 | GDYEVDYGMDV | 3 | QQFNSYPWT | 6 |

TABLE 2

Amino Acid Sequence SEQ ID NOs. of Antibody 1

|  | Heavy Chain | | | Light Chain | | |
|---|---|---|---|---|---|---|
|  | Variable region | Complete Without signal | Complete With signal | Variable region | Complete Without signal | Complete With signal |
| Antibody 1 | 7 | 9 | 11 | 8 | 10 | 12 |

Enzyme-Linked Immunosorbent Assay (ELISA) Binding Assay

For the CSF-1R binding assay, coat a 96-well plate with soluble recombinant human-CSF-1R-Fc fusion protein (R&D Systems) (1 μg/mL×100 μL) seal plate, and incubate overnight at 4° C. Wash the wells 3 times with PBS (Phosphate Buffered Saline) containing 0.2% TWEEN-20® (PBS/T), then block wells for 1 hour at room temperature (20-25° C.) (RT) with PBS containing 3% bovine serum albumin (BSA). Aspirate the BSA-PBS mixture and wash plates 3 times with PBS/T. Make serial dilutions of Antibody 1 or control IgG (starting at 3 μg/mL and diluting 3-fold) and add 100 μL to wells for 1 hour at RT. Wash wells three times with PBS/T. After washing, incubate the plate with 100 μL of an anti-human F(ab')$_2$ fragment specific-HRP conjugate (Jackson ImmunoResearch) in PBS (1:5000 dilution) at RT for 1 hour. Wash the plates 5 times with PBS/T and then incubate with 100 μL of a 1:1 preparation of TMB peroxidase substrate and peroxidase solution B (KPL) for 15 minutes at RT. Stop the colorometric reaction with the addition of 100 μL of 0.1 M H$_2$SO$_4$. Collect data using a microplate reader set at 450 nm. Analyze the absorbance data with GraphPad Prism software to calculate the ED$_{50}$. ED$_{50}$, or the half maximal effective dose, is the dose necessary to achieve 50% maximal binding.

The ED$_{50}$ of Antibody 1 to human CSF-1R is $8.7 \times 10^{-11}$M, reported as 0.09 nM. Antibody 1 exhibits strong binding to CSF-1R.

Enzyme-Linked Immunosorbent Assay (ELISA) Blocking Assay
ELISA to Show Antibodies Block the CSF-1/CSF-1R Interaction Coat a 96-well microtiter plates with (0.5 μg/mL×100 μL) CSF-1 (R&D Systems) at 4° C. overnight. Wash the wells 3 times with PBS/T, then block with 100 μL, 3% BSA/PBS for 1 hour at RT. Wash again 3 times with PBS/T. Dilute soluble human rh-CSF-1R-Fc fusion protein (R&D Systems) to a final concentration of 0.250 µg/mL in PBS. Concurrently, dilute Antibody 1 in PBS to a final concentration of 200 nM. Serially dilute Antibody 1 in 1:3 increments from the initial 200 nM down to $3 \times 10^{-12}$ M. Combine 100 µL of the rh-CSF-1R-Fc with 100 µL of each dilution of Antibody 1 for 30 minutes at RT. Incubate 100 µL of Antibody 1:CSF-1R-Fc mixtures for 1 hour at RT in the CSF-1-coated wells. After 1 hour of incubation at RT, wash 3 times with PBS/T and add a 1:5000 dilution of the anti-human IgG-Fc-HRP conjugated antibody to the plates for 1 hour at RT. Wash the plates 5 times with PBS/T and then incubate with 100 µL of a 1:1 preparation of TMB peroxidase substrate and peroxidase solution B (KPL) for 15 minutes at RT. Stop the colorometric reaction with the addition of 100 µL of 0.1 M $H_2SO_4$. Collect data using a microplate reader set at 450 nm. Analyze the absorbance data with GraphPad Prism software to calculate the $IC_{50}$. $IC_{50}$, or the half maximal inhibitory concentration, is the concentration of the antibody causing 50% inhibition of ligand binding to the receptor.

The $IC_{50}$ of Antibody 1 binding to human CSF-1R is $8.1 \times 10^{-10}$ M, reported as 0.81 nM. Antibody 1 inhibits CSF-1 binding to CSF-1R, thereby preventing CSF-1R activation by the CSF-1 ligand.

ELISA to Show Antibodies Block the IL-34/CSF-1R Interaction

Coat a 96-well microtiter plates with (0.5 µg/mL×100 µL) IL-34 (R&D Systems) at 4° C. overnight. Wash the wells 3 times with PBS/T, then block with 100 µL 3% BSA/PBS for 1 hour at RT. Wash again with 3 times PBS/T. Dilute soluble human rh-CSF-1R-Fc fusion protein (R&D Systems) to a final concentration of 0.250 µg/mL in PBS. Concurrently, dilute Antibody 1 in PBS to a final concentration of 200 nM. Serially dilute Antibody 1 in 1:3 increments from the initial 200 nM down to $3 \times 10^{-12}$ M. Combine 100 µL of the rh-CSF-1R-Fc with 100 µL of each dilution of Antibody 1 for 30 minute at RT. Incubate 100 µL of Antibody 1-CSF-1R-Fc mixtures for 1 hour at RT in the IL-34-coated wells. After 1 hour of incubation at RT, wash 3 times with PBS/T and add a 1:5000 dilution of the anti-human IgG-Fc-HRP conjugated antibody to the plates for 1 hour at RT. Wash the plates 5 times with PBS/T and then incubate with 100 µL of a 1:1 preparation of TMB peroxidase substrate and peroxidase solution B (KPL) for 15 minutes at RT. Stop the colorometric reaction with the addition of 100 µL of 0.1 M $H_2SO_4$. Collect data using a microplate reader set at 450 nm. Analyze the absorbance data with GraphPad Prism software to calculate the $IC_{50}$. $IC_{50}$, or the half maximal inhibitory concentration, is the concentration of the antibody causing 50% inhibition of ligand binding to the receptor.

The $IC_{50}$ of Antibody 1 binding to human CSF-1R is $7.0 \times 10^{-10}$ M, reported as 0.71 nM. Antibody 1 inhibits IL-34 binding to CSF-1R, thereby preventing CSF-1R activation by the IL-34 ligand.

Binding Kinetics Analysis by Surface Plasmon Resonance/ Biacore® Analysis

Measure the binding kinetics of Antibody 1 to CSF-1R-Fc at 25° C. on a Biacore® 2000 SPR Biosensor (GE Healthcare) Immobilized soluble CSF-1R-Fc fusion protein (concentration of 10 µg/mL and pH 5), ranging from 395 to 1200 response units, on a CMS chip using the standard amine coupling protocol. Use HBS-EP (0.01 M HEPES (pH 7.4), 0.15 mM NaCl, and 3 mM EDTA, 0.005% v/v Surfactant P20) as a running buffer during binding affinity measurements. Perform interaction analyses as the antibodies in solution are injected at concentrations ranging from 1.5-100 nM over the prepared surface of the CMS sensor chip. Inject the antibodies over 3 minutes for binding and allow to dissociate for 15 minutes. Perform regeneration of the immobilized protein by a 10 µL/min injection of 20 mM HCL. Use BIAevaluation version 4.1 software to determine the $K_a$ ($k_{on}$) and $K_d$ ($k_{off}$) of the complex formation by simultaneous global fitting of the data to a 1:1 Langmuir model. Calculate the equilibrium association constant ($K_A$) from the ratio of $1/K_D$ measured in Molar (1/M). Calculate the equilibrium dissociation constant ($K_D$) from the ratio of rate constants $K_d/K_a$ measured in Molar (M).

The average $K_a$, $K_d$, and $K_D$ values for multiple Biacore® analyses for Antibody 1 with human CSF-1R are summarized in Table 3.

TABLE 3

Binding Kinetics of Antibody to Recombinant Human CSF-1R

| Antibody | $K_a$ (1/Ms) $K_{on}$ | $K_d$ (1/s) $K_{off}$ | $K_D$ (M) |
|---|---|---|---|
| Antibody 1 | $3.7 \times 10^5$ | $3.3 \times 10^{-4}$ | $8.0 \times 10^{-10}$ |

Antibody 1 demonstrates a high binding affinity to CSF-1R.

Phosphorylation of CSF-1R Detected by Western Blot

Seed NIH3T3 cells stably transfected with CSF-1R cells in a 12-well plate at a density of $5 \times 10^5$ cells/well in 1 mL well of Dulbecco's Modified Eagles Medium (DMEM) containing 10% fetal bovine serum (FBS) and 1 mg/mL geneticin for 5 hours. Wash monolayers twice in PBS and culture overnight in 0.9 mL/well DMEM with 1% FBS. Make serial dilutions of Antibody 1 in DMEM (starting at 1 µg/mL and diluting 3-fold) and add 100 µL to wells for 2 hours at 37° C. Stimulate cells with 100 ng/mL CSF-1 or IL-34 ligand for 10 minutes and then place on ice and wash with ice-cold PBS. Lyse the cells in 100 µL of 50 mM Hepes (pH 7.5 150 mM NaCl, 0.5% Triton X-100, 1 mM $Na_3VO_4$, 10 mM NaPPi, 50 mM NaF) and tablet of protease inhibitors (Roche) on ice for 10 minutes. Clarify the lysed cells by centrifugation at 4° C. Load 20 µL lysate on a denaturing electrophoresis gel and blot onto a nitrocellulose membrane. Detect tyrosine-phosphorylated CSF-1R on the blot by using an anti-phosphoCSF-1R antibody at 1 µg/mL (Cell Signaling). Determine CSF-1R signaling by probing the blot with either anti-phospho-MAPK (1:500 dilution) or anti-phopho-Akt (1:1000) (Cell Signaling). To insure equal loading of the lanes, probe blots with anti-CSF-1R antibodies (1 µg/mL; R&D Systems) or anti-actin antibodies (1:2000; Sigma). Incubate all primary antibodies with rocking for 1 hour at RT; followed by the corresponding secondary antibody conjugated with HRP, also with rocking for 1 hour at RT. Visualize bands with a chemiluminescence reagent (GE Healthcare).

NIH-3T3 cells stably transfected with CSF-1R show rapid phosphorylation of CSF-1R when stimulated with either CSF-1 or IL-34. The presence of Antibody 1 inhibits CSF-1R phosphorylation, even when levels of Antibodies are at 1 nM, indicating that the binding of Antibody 1 to CSF-1R prevents activation of the receptor by either CSF-1 or IL-34. Inhibition of CSF-1R phosphorylation also leads to diminished phosphorylation of the signaling molecules used by the either the CSF-1 or IL-34 pathway. Both Akt and MAPK, which are downstream of CSF1-R, have decreased phosphorylation levels when cells are incubated with 100 nM to 1 nM of Antibodies 1. Therefore, Antibody 1 prevents CSF-1R activation and the activation of the kinase cascade that follows CSF-1R stimulation. There was no difference in the protein levels of actin and CSF-1R between lanes, as evidenced by equal chemiluminescent signal in each lane seen when the blots were probed with antibodies against these molecules. Hence, the inhibition of CSF-1R phosphorylation is not due to technical difficulties with uneven loading of protein samples but a true representation of decreased signaling.

Internalization and Degradation Assays

Antibody 1 Induces Internalization of the CSF-1R Receptor

Plate NIH-3T3-CSF-1R cells on 8-well chambered slides (Nunc) and incubate at 37° C. until cells cover 50% of the surface area of the wells. Allow the slides to cool to 4° C. before the start of the experiment in a water:ice slurry mixture. Incubate cells with 5 µg/mL Antibody 1 and immediately transfer to 37° C. for 15 minutes to 4 hours to allow internalization to occur. Continue incubating a separate set of slides in the water:ice slurry mixture for 15 minutes to 4 hours with 5 µg/mL Antibody 1 as a control. The 4° C. incubation prevents internalization of the CSF-1 receptor, therefore any signal seen within the cell is an artifact. After incubation, wash cells twice with cold PBS before fixing the cells with ice-cold 1% paraformaldehyde for 15 minutes. After washing three times with cold PBS, permeabilize cells in PBS containing 0.5% saponin and 1% BSA for 5 minutes and then wash again in PBS containing 1% BSA. Label with goat Cy3 anti-human IgG (1:5000 dilution) for 1 hour to fluorescently label Antibody 1. Perform three final washes with PBS before mounting in GelMount (Biomeda) and covering the slides with coverglass. The fluorescently labeled Antibody 1 can be visualized microscopically to determine cellular localization under the various conditions described above.

Upon microscopic inspection, Antibody 1 is seen on the periphery of the cell at 4° C. before the start of the experiment. Switching the cells to 37° C. allows rapid internalization of the Antibody 1/CSF-1R complex, usually seen within 15 minute. After 1 or 2 hours of incubation with Antibody 1, all antibody/CSF-1R complexes are perinuclear with very little visualized on the plasma membrane, indicating that Antibody 1 binding to CSF-1R induces the receptor to internalize rapidly and remain inside the cell. Cells kept at 4° C. for up to 2 hours show only peripheral staining of the cell, with no internalization of Antibody 1. Thus, internalization of the antibody/CSF-1R is an ATP-dependent process that occurs within 15 minutes of antibody addition to the cells.

Antibody 1 Induces Degradation of the CSF-1R Receptor

Seed NIH-3T3-CSF-1R cells at $5\times10^5$ cells/well in a 12 well plate in 1 mL DMEM media containing 10% FBS and 1 mg/mL geniticin. After incubating cell at 37° C. for 5 hours, add either 100 ng/mL CSF-1 or 15 ng/mL Antibody 1 to the plates. CSF-1 is known to induce internalization and degradation of CSF-1R, thereby acting as a positive control for the experiment. Allow CSF-1 to remain on cells for 1 and 5 hours before collecting cells. In the other wells, incubate for 24 and 48 hours with Antibody 1 before collecting cells. Aspirate medium, lyse cells and run clarified lysates on gels (as described above). Probe transferred proteins with anti-CSF-1R antibodies to determine the amount of receptor for each condition. Probe the same blots with anti-actin antibodies to normalize protein levels. Quantify CSF-1R and actin levels using the Multi-Gauge program to measure band density on the Western blot. The relative total CSF-1R protein level is represented by the total CSF-1R band density divided by the corresponding actin band density.

CSF-1 incubation with NIH-3T3-CSF-1R cells leads to degradation of CSF-1R within 1 hour of treatment and CSF-1R levels are halved by 5 hours. Degradation of CSF-1R when incubated with Antibody 1 is not as pronounced; Antibody 1 decreases CSF-1R levels by one quarter. After 48 hours, degradation levels remain the same, indicating that the degradation rate remains constant. Therefore, Antibody 1 binding to CSF-1R leads to the degradation of the receptor in cells.

Antibody-Dependent Cell-Mediated Cytotoxicity (ADCC) by Antibody 1

Besides inhibiting CSF-1 binding to CSF-1R and inducing internalization and degradation of CSF-1R, Antibody 1 also inhibits CSF-1R by triggering an ADCC response.

NKM-1 human leukemia cells are seeded at $2\times10^5$ cells/mL in 25 µL RPMI media containing 10% Ultra-Low IgG FBS and 3 ng/mL of human IL-2 in a 96 well plate. Make 1:3 serial dilutions of 1 µg/mL Antibody 1 in either an IgG1 or IgG2 backbone, adding 25 µL/well. After a 15 minute incubation, seed 25 µL of $3\times10^6$ cells/mL human NK cells (Lonza) and incubate for an additional four hours at 37° C. Add 10 µL of Lysis Buffer from aCella-TOX kit (Cell Technology) and bring to RT for 15 minutes. Add 125 µL of low IgG FBS and centrifuge plates for 1 minute at 750×g. In Optiplates (Perkin Elmer), add 50 µL Enzyme Assay Diluent from aCella-TOX kit and carefully transfer 50 µL of cell supernatant to Optiplates. Prepare enzyme assay reagent and detection reagent according to kit instructions, adding 100 µL enzyme assay reagent immediately followed by 50 µL of detection reagent to Optiplates. Read plates in luminometer 20 minutes after reagents are added.

ADCC activity increases in an Antibody 1 dose-dependent manner with 9% of NKM-1 cells killed when Antibody 1 concentrations reach 1 µg/mL. In contrast, when Antibody 1 is cloned into an IgG2 backbone there is no change in ADCC activity with increasing amounts of Antibody 1. Therefore Antibody 1, an IgG1 molecule, induces ADCC of cells to which it binds.

Epitope Mapping

Previous publications have determined that CSF-1 binds to the first three Ig domains of CSF-1R. Wang et al., Mol. Cell. Biol. 13: 5348 (1993). Antibody 1 binds CSF-1R and inhibits CSF-1 binding to human CSF-1R, thus it must bind on or near the first three Ig domains of CSF-1R. To determine which epitopes Antibody 1 binds to on the CSF-1R molecule, the first three Ig domains of mouse and human are swapped (see Table 4). Antibody 1 does not recognize the mouse CSF-1R therefore, if a mouse Ig domain is inserted in a critical binding region of the human CSF-1R, binding of the antibodies would not occur.

Insert the modifications of the first three Ig domains into a human CSF-1R backbone containing the remaining two most C-terminal Ig domains of the extracellular domain. Fuse these constructs to the Fc portion of an IgG molecule for ease in protein production and stability of the molecules.

TABLE 4

CSF-1R Ig Domains Defined

| Ig Domain | Amino Acid No. |
|---|---|
| 1 | 21-107 |
| 2 | 108-201 |
| 3 | 202-292 |
| 4 | 293-402 |
| 5 | 401-512 |

Chimera 1 thus contains mouse Ig domain 1, human Ig domain 2 and human Ig domain 3 (m,h,h), human Ig domains 4 and 5 fused to an Fc tag. Chimera 2 to chimera 7 are as follows: m,m,h (chimera 2), m,m,m (chimera 3), h,m,h (chimera 4), h,m,m (chimera 5), h,h,m (chimera 6) and m,h,m (chimera 7) fused to the last two Ig domains of human CSF-1R and then the Fc tag.

Antibody 1 binding to the chimeric CSF-1R proteins is determined by binding ELISAs and Biacore® as described above. Briefly, coat plates with 100 μL of 200 ng/mL human, mouse or chimera 1-7 proteins overnight. After washing and blocking the plates, add Antibody 1 in replicates at 100 nM concentration. Add anti-human Fab secondary antibodies conjugated to HRP at a concentration of 1:10,000 to detect Antibody 1 binding to the CSF-1R molecules.

As expected, Antibody 1 binds to the human but not mouse CSF-1R in the ELISA binding assays. Antibody 1 binds weakly to chimeras containing the first or second human Ig domains, but not those that contain the first or second mouse Ig domain. Antibody 1 binds strongly to the chimera that contains both the first and second Ig domain of human CSF-1R. All other constructs do not bind Antibody 1. Therefore, Antibody 1 binds to Ig domains one and two, but requires both domains for strong antibody binding to human CSF-1R when evaluated in a binding assay. Biacore® data recapitulates the ELISA data. Any chimeric construct that did not contain a human second Ig domain did not bind Antibody 1 even when antibody levels were at 1 μM, indicating that the second Ig domain is required for Antibody 1 binding. Antibody 1 binding was further enhanced when the first Ig domain was also of human origin. Therefore, Antibody 1 primarily binds to the second Ig domain of CSF-1R but has some beneficial contacts with the first Ig domain.

Differentiation and Proliferation Assays
Macrophage Differentiation by CSF-1

Seed monocytes (Lonza) at a density of 4×10^5 cells/mL in each chamber of an 8-chamber slide in 900 μL Roswell Park Memorial Institute (RPMI) 1640 media containing 10% FBS and 100 ng/mL hCSF-1. Make serial dilutions of Antibody 1 in RPMI (starting at 1 μg/mL and diluting 3-fold) and add 100 μL to the wells. Incubate at 37° C., changing media every three days until monocytes are visibly seen to adhere to the plate and elongate, which is characteristic of macrophage differentiation.

Monocytes treated with 2 nM or higher concentrations of Antibody 1 in the presence of CSF-1 fail to differentiate into macrophages, retaining their rounded morphology characteristic of monocytes. CSF-1 induction of monocyte to macrophage differentiation can be inhibited with Antibody 1 with an $IC_{50}$ of 0.25 nM. In addition, many die during treatment, unable to survive without continual stimulation with CSF-1.

Macrophage Differentiation by IL-34

Seed monocytes (Lonza) at a density of 4×10^5 cells/mL in each chamber of an 8-chamber slide in 900 μL Roswell Park Memorial Institute (RPMI) 1640 media containing 10% FBS and 100 ng/mL hIL-34. Make serial dilutions of Antibody 1 in RPMI (starting at 1 μg/mL and diluting 3-fold) and add 100 μL to the wells. Incubate at 37° C., changing media every three days until monocytes are visibly seen to adhere to the plate and elongate, which is characteristic of macrophage differentiation.

Monocytes treated with 2 nM or higher concentrations of Antibody 1 in the presence of IL-34 fail to differentiate into macrophages, retaining their rounded morphology characteristic of monocytes. IL-34 induction of monocyte to macrophage differentiation can be inhibited with Antibody 1 with an $IC_{50}$ of 0.3 nM. In addition, many die during treatment, unable to survive without continual stimulation with CSF-1.

Monocyte Proliferation by CSF-1

Seed monocytes (Lonza) at a density of 3000 cells/well in a 96-well plate in the presence of RPMI 1640 media containing 10% FBS and 100 ng/mL CSF-1. The following day, exchange media and add Antibody 1 serially diluted from 20 nM to 0.01 nM (1:3 fold dilutions). Exchange media for fresh media containing 10% FBS, 100 ng/mL CSF-1, and antibody three days later and allow cells to grow an additional 5 days. Upon addition of 100 μL of CellTiter Glo Luminescent buffer and substrate (Promega), shake cells for 10 minutes and read luminescence as an indicator of viability.

The $IC_{50}$ of Antibody 1 inhibiting 50% of monocyte growth is $1.4\times10^{-10}$ M, reported as 0.1 nM. The $IC_{50}$ for CSF-1 induction of monocyte growth in the presence of Antibody 1 indicates that Antibody 1 inhibits proliferation of monocytes in culture.

Monocyte Proliferation by IL-34

Seed monocytes (Lonza) at a density of 3000 cells/well in a 96-well plate in the presence of RPMI 1640 media containing 10% FBS and 100 ng/mL IL-34. The following day, exchange media and add Antibody 1 serially diluted from 20 nM to 0.01 nM (1:3 fold dilutions). Exchange media for fresh media containing 10% FBS, 100 ng/mL IL-34, and antibody three days later and allow cells to grow an additional 5 days. Upon addition of 100 μL of CellTiter Glo Luminecent buffer and substrate (Promega), shake cells for 10 minutes and read luminescence as an indicator of viability.

The $IC_{50}$ of Antibody 1 inhibiting 50% of monocyte growth is 0.5 nM. The $IC_{50}$ for IL-34 induction of monocyte growth in the presence of Antibody 1 indicates that Antibody 1 inhibits proliferation of monocytes in culture.

Proliferation Assay for Tumor Cell Lines with CSF-1

Seed NKM-1 leukemia cells at 1×10^4 cells/mL in 100 μL RPMI 1640 media containing 1% FBS in a 96 well plate overnight. Add 20 ng/mL of CSF-1 to cells in RPMI 1640 media containing 1% FBS and 20 nM to 0.01 nM serially diluted Antibody 1 (1:3 fold dilutions). Incubate for an additional 3 days at 37° C. Upon addition of 100 μL of CellTiter Glo Luminecent buffer and substrate (Promega), shake cells for 10 minutes before reading luminescence (as an indicator of viability).

The $IC_{50}$ for NKM-1 growth in the presence of Antibody 1 is $7.6\times10^{-11}$ M, reported as 0.07 nM. This indicates that Antibody 1 inhibits proliferation of NKM-1 cells in culture.

In Vivo Tumor Models wherein CSF-1R is Expressed on the Surface of the Tumor

Prolonged Survival of NKM-1 Human Leukemia-Bearing Mice Treated with Antibody 1

Irradiate Nu/nu mice sublethally with 200 rads/mouse 24 hours before intravenous injection with 2.5×10^6 NKM-1 leukemia cells. A further 24 hours later, randomly divide mice into 4 groups receiving either 60 mg/kg human IgG, 60 mg/kg, 20 mg/kg or 5 mg/kg Antibody 1 twice weekly. Monitor mice daily for survival. Determine P values by log rank Mantel Cox test.

TABLE 5

Increased Survival Of Mice Treated With Antibody 1 Bearing NKM-1 Leukemia Cells

| Treatment | Median survival (days) | Cohort comparison | P value relative to control |
|---|---|---|---|
| Human IgG | 35 | N/A | N/A |
| Antibody 1 (5 mg/kg) | 55 | Human IgG control | <0.0001 |
| Antibody 1 (20 mg/kg) | 46 | Human IgG control | <0.0001 |
| Antibody 1 (60 mg/kg) | 46 | Human IgG control | <0.0001 |

N/A = Not Applicable

Tumor volumes are calculated by the formula Volume=[(Pi/6)1×w$^2$], wherein Pi equals 3.14, w represents width and 1 represents length. Percent of Control or % T/C=100*(Treatment Volume)/(Control Volume). Statistical significance was ascribed if the p-value was less than or equal to 0.05.

Antibody 1 increases the survival of mice bearing NKM-1 leukemia cells as seen in Table 5.

In Vivo Tumor Models wherein CSF-1R is Expressed on the Surface of Tumor-Associated Macrophages Anti-CSF-1R Antibody 1 is a fully human antibody that recognizes the human form of CSF-1R but not the murine form of the receptor. Therefore, an anti-mouse antibody is required to conduct proof of concept in vivo studies wherein CSF-1R is expressed on the macrophage. These studies address the role of mouse macrophages on the growth of human tumors in mice xenograft models. An anti-mouse antibody would affect the mouse macrophages but not the tumor, allowing the ability to gauge the effect of stromal macrophages on tumor growth. The following experiments are conducted with Antibody 2, a rat-anti-mouse CSF-1R antibody.

Efficacy of the Anti-Mouse CSF-1R mAb in the AN3CA Xenograft Model of Human Endometrial Carcinoma Subcutaneously inject Nu/nu mice (female, 7-8 weeks of age) with 5×10$^6$ AN3CA cells/mouse into the left flank. When tumors reach approximately 200 mm$^3$, randomize mice into groups of 12 mice/treatment.

Prepare Antibody 2 and Rat IgG in saline at a concentration of 6 mg/mL and administer subcutaneously three times a week at 40 mg/kg. On day 15 record tumor volumes and calculate % T/C. Analyze tumor volumes using RM ANOVA. A T/C % of 66% is calculated for the treatment group with Antibody 2 versus the Rat IgG control group. These results show significant tumor inhibition (p=0.045) in animals treated with Antibody 2.

Efficacy of the Anti-Mouse CSF-1R mAb in the HCC1954 Xenograft Model of Human Breast Carcinoma Inject Nu/nu (female, 7-8 weeks; Charles River Laboratories) mice subcutaneously with 1×10$^7$ HCC1954 cells/mouse. When tumors reach 300 mm$^3$ in size, randomize mice by tumor size, allocating 12 animals to each treatment group. Prepare rat IgG and Antibody 2 in saline at a concentration of 6 mg/mL and administer subcutaneously, three times a week. Dose rat IgG animals at 40 mg/kg and dose Antibody 2 animals with either 40 mg/kg or 10 mg/kg at each injection. Record tumor measurements twice weekly; 37 days after first injection calculate the T/C %. Analyze tumor volumes using RM ANOVA.

As shown in Table 6, a T/C % of 77% was calculated for the treatment group receiving 10 mg/kg and T/C % of 56% for the treatment group receiving 40 mg/kg on day 37 as the ratio of the relative tumor volumes versus the saline control group. The results show significant tumor inhibition (p=0.0014) in animals treated with 40 mg/kg Antibody 2.

Antitumor Effect of an Anti-Mouse CSF-1R mAb in the DU145 Human Prostate Xenograft Model Subcutaneously inject Nu/nu mice (male, 7-8 weeks of age) with 15×10$^6$ DU145 cells/mouse into the left flank. When tumors reach approximately 250 mm$^3$, randomize mice into groups of 12 mice/treatment.

Prepare Antibody 2 and Rat IgG in saline at a concentration of 6 mg/mL and administer subcutaneously three times a week at 40 and 10 mg/kg. On day 21 record tumor volumes and calculate % T/C for the 10 mg/kg and 40 mg/kg. Analyze tumor volumes using RM ANOVA.

As shown in Table 6, a T/C % of 50 and 43 is calculated treatment groups 10 mg/kg and 40 mg/kg respectively versus the Rat IgG control group. These results show significant tumor inhibition (p=<0.0001 for both concentrations) in animals treated with Antibody 2.

TABLE 6

Inhibition of Human Tumor Xenografts by Antibody 2

| Model Description | Treatment | % T/C | Cohort Comparison | P value relative to control |
|---|---|---|---|---|
| HCC1954 (breast) | Antibody 2 (10 mg/kg) | 77 | Rat IgG control | 0.4543 |
| HCC1954 (breast) | Antibody 2 (40 mg/kg) | 56 | Rat IgG control | 0.0014 |
| DU145 (prostate) | Antibody 2 (10 mg/kg) | 50 | Rat IgG control | <0.0001 |
| DU145 (prostate) | Antibody 2 (40 mg/kg) | 43 | Rat IgG control | <0.0001 |

Decreased Macrophage Infiltration in HCC1954 Breast and DU145 Prostate Tumors Treated with an Anti-Mouse CSF-1R mAb Remove tumors from the animals in the HCC1954 (breast) and DU145 (prostate) animal studies described above. Cut tumor along the longest axis and place in 10% formalin overnight at 4° C. while rocking. After 24 hours, wash 2 times in PBS over 20 minutes, then add solutions of progressively higher concentrations of ethanol, until the tumor is in 100% ethanol. Exchange the ethanol for xylene by several incubations in 100% xylene and embed the tumor in paraffin. Section paraffin blocks at 4 μm and place on glass slides. Deparaffinize and rehydrate tissue by progressive incubations in xylene followed by increasing concentrations of water in ethanol. Heat tumor slides in target retrieval solution (Dako) for 3 minutes in microwave before blocking endogenous peroxidases with 3% $H_2O_2$ for 10 minutes at RT. Block non-specific protein binding with Protein Block (Dako) for 10 minutes before adding rat anti-mouse macrophage-specific antibody, F4/80 (2 μg/mL; Serotec) conjugated to biotin and incubate overnight at 4° C. Incubate in HRP-Streptavidin (1:1000 dilution; Jackson ImmunoResearch) for 45 minutes at RT and wash 3 times. Develop in DAB (Dako) per kit instructions, stopping the reaction with two washes in water. Counterstain briefly with Mayer's Hematoxylin (10 minutes; Dako) followed by a water wash, acid alcohol dip, a second water wash and bluing using ammonia water. Dehydrate, clear and coverslip using a permanent mounting medium. Analyze 5 images from three animals for each treatment group. Using ImagePro software, determine the number of macrophages/area for each treatment group.

TABLE 7

Macrophage Infiltration in Tumors Treated with an Anti-Mouse CSF-1R mAb Antibody 2

| Model Description | Treatment | Avg. Macrophage No./Area | Cohort Comparison | P value relative to control |
|---|---|---|---|---|
| HCC1954 (breast) | Rat IgG | 664 | N/A | N/A |
| HCC1954 (breast) | Antibody 2 (10 mg/kg) | 82 | Rat IgG control | <0.0001 |
| HCC1954 (breast) | Antibody 2 (40 mg/kg) | 76 | Rat IgG control | <0.0001 |
| DU145 (prostate) | Rat IgG | 84 | N/A | N/A |

TABLE 7-continued

Macrophage Infiltration in Tumors Treated
with an Anti-Mouse CSF-1R mAb Antibody 2

| Model Description | Treatment | Avg. Macrophage No./Area | Cohort Comparison | P value relative to control |
|---|---|---|---|---|
| DU145 (prostate) | Antibody 2 (10 mg/kg) | 5 | Rat IgG control | <0.0001 |
| DU145 (prostate) | Antibody 2 (40 mg/kg) | 0.5 | Rat IgG control | <0.0001 |

N/A = Not Applicable

As seen in Table 7, macrophage numbers are decreased in both tumor models, especially along the periphery. Thus, Antibody 2 treatments lead to a decrease in macrophage infiltration of the tumors, indicating that the anti-mouse CSF-1R antibody is responsible for depleting the macrophage population in these tumors.

Significance of Macrophages and CSF-1 Levels on Tumor Progression

In addition to breast and prostate, inhibition of tumor growth, as well as the treatment of many cancers can be beneficially effected by the administration of Antibody 1. Some tumor types such as renal cancer express CSF-1R on their cell surface and could be directly inhibited from growing with Antibody 1 treatment (Soares, et al., Modern Pathol. 22: 744-752 (2009)). Other tumor types such as Hodgkin's lymphoma and multiple myeloma, which have a large tumor-associated macrophage population could benefit from Antibody 1 treatment, where Antibody 1 could eliminate the macrophages that are inducing tumor growth (Steidl, et al. New Engl. J. Med. 362: 875-885 (2010); Zheng, et al., Blood 114: 3625-3628 (2009)). Additionally, tumors that secrete CSF-1 are sensitive to anti-CSF-1 or CSF-1R treatment, such as colorectal cancer (Aharinejad, et al., Cancer Res. 62: 5317-5324 (2002)) and would be appropriate for Antibody 1 treatment. Moreover, ovarian cancer, hepatocellular carcinoma and renal cell carcinomas, whose high CSF-1 expression correlates with poor prognosis would all be candidates for Antibody 1 treatment (Toy, et al., Gyn. Oncol. 80: 194-200 (2001); Zhang, et al., Gyn. Oncol. 107: 526-531 (2007); Zhu, et al., J. Clin. Oncol. 26: 2707-2716 (2008); Gerharz, et al., Urol. 58: 821-827 (2001)).

Non-CSF-1R Expressing Tumors that Possess Tumor-Associated Macrophages are Growth Inhibited by Anti-CSF-1R Antibodies Only if CSF-1 Secreting Seed tumor cell lines HCC1954 (breast), DU145 (prostate) and Pc3 (prostate) at $5 \times 10^5$ cells/mL for 48 hours in growth medium containing 1% FBS. Collect, clarify, and analyze the medium using a R&D Quantikine Human M-CSF Assay Kit (R&D Systems). Determine CSF-1 levels at time 0 and 48 h as pg/mL.

At 0 hours, as expected, there was no discernable CSF-1 in the media. However, within 48 hours, the HCC1954 cells secreted 3613 pg/mL of CSF-1 while the DU145 cells produced 4019 pg/mL. In contrast, the Pc3 cells media only contained 39 pg/mL of CSF-1.

The Prostate Cell Line Pc3 is Grown in Mice to Verify if Lack of CSF-1 Expression is Correlated with Resistance to Anti-CSF-1R Treatment Inject $5 \times 10^6$ Pc3 prostate cells subcutaneously into nude mice (male, 7-8 weeks of age) and allow tumors to reach 300 mm$^3$ before subdividing into treatment groups of 12 mice each. Dose animals with either 40 mg/kg of Rat IgG, 40 mg/kg Antibody 2 or 10 mg/kg Antibody 2 three times a week until control tumors reach 2000 mm$^3$ Measure tumor volumes and calculate the T/C % for each treatment group on day 18 as the ratio of the relative tumor volumes versus the Rat IgG control group. Analyze tumor volumes using RM ANOVA.

TABLE 8

Correlation of CSF-1 and Resistance to Anti-CSF-1R Treatment

| Treatment | T/C % | Cohort Comparison | P value relative to control |
|---|---|---|---|
| Antibody 2 (10 mg/kg) | 101 | Rat IgG control | 0.95 |
| Antibody2 (40 mg/kg) | 102 | Rat IgG control | 0.53 |

There is no difference in growth between the Rat IgG treated control groups versus the Antibody 2 treated groups, indicating that elevated CSF-1 levels may be a biomarker for treatment with anti-CSF-1R antibodies.

CSF-1 Secretion is Correlated to Sensitivity of Anti-CSF-1R Treatment when CSF-1R is Expressed on the Surface of Tumor-Associated Macrophages Inject cells, as detailed in Tables 9 and 10 below, subcutaneously into nude mice and allow tumors to reach 300 mm$^3$ before subdividing into treatment groups of 12 mice each. Dose animals according to the treatment regiment detailed in Tables 9 and 10 below three times a week until control tumors reach 2000 mm$^3$ Measure tumor volumes and calculate the T/C % for each treatment group as the ratio of the relative tumor volumes versus the Rat IgG control group. Analyze tumor volumes using RM ANOVA.

TABLE 9

Sensitivity in CSF-1 Secreting Tumor Models

| Model Description | Tumor Type | Species | Treatment | % T/C | Cohort Comparison | P value relative to control |
|---|---|---|---|---|---|---|
| MDA-MB-231 LS-OP-PT | Breast | Human | 40 mg/kg TIW | 51 | Rat IgG control | 0.0002 |
| HCC-1954 | Breast | Human | 40 mg/kg TIW | 56 | Rat IgG control | 0.0014 |
| DU145 | Prostate | Human | 40 mg/kg TIW | 43 | Rat IgG control | <0.0001 |
| 4T1 | Breast | Mouse | 40 mg/kg TIW | 54 | Rat IgG control | 0.0001 |
| EMT6 | Breast | Mouse | 40 mg/kg TIW | 42 | Rat IgG control | <0.0001 |

TIW = Three time a week.

TABLE 10

Sensitivity in Non-CSF-1 Secreting Tumor Models

| Model Description | Tumor Type | Species | Treatment | % T/C | Cohort Comparison | P value relative to control |
|---|---|---|---|---|---|---|
| MCF-7 | Breast | Human | 60 mg/kg BIW | 70 | Rat IgG control | 0.0166 |
| JimT1 | Breast | Human | 40 mg/kg TIW | 93 | Rat IgG control | 0.23 |
| PCS | Prostate | Human | 40 mg/kg TIW | 102 | Rat IgG control | 0.53 |

TIW = Three time a week.

CSF-1 secreting tumors (Table 9) all respond to anti-CSF-1R treatment with Antibody 2 while those tumors that do not secrete CSF-1 (Table 10) did not respond or only poorly to anti-CSF-1R Antibody 2. CSF-1 secretion is correlated to sensitivity of anti-CSF-1R treatments in tumor models wherein CSF-1R is expressed on the surface of tumor-associated macrophages. Accordingly, elevated CSF-1 levels function as a potential sensitivity indicator or biomarker when CSF-1R is expressed on the surface of tumor-associated macrophages.

CSF-1R can also be expressed on the surface of tumor cells. CSF-1 secretion is not correlated to sensitivity of anti-CSF-1R treatments for CSF-1R tumor cell surface expression.

IL-34 Levels in Tumors and Patient Sera Samples

In addition to CSF-1, IL-34 can also bind to CSF-1R, induce phosphorylation of the receptor, and activate downstream signaling molecules, which lead to macrophage differentiation and survival. Both CSF-1 and IL-34 bind to the IgG domains in the extracellular region of CSF-1R (Lin, et al., Science, 320: 807-11 (2008)) and both ligands can be inhibited from binding to CSF-1R by Antibody 1 ($IC_{50}$=0.81 nM and $IC_{50}$=0.71 nM for inhibition of CSF-1 and IL-34 binding by Antibody 1, respectively as discussed supra). Treatment of NIH-3T3 cells stably transfected with CSF-1R with Antibody 1 inhibits phosphorylation of CSF-1R by IL-34 (as discussed supra). Furthermore, IL-34 induction of monocyte to macrophage differentiation and macrophage proliferation can be inhibited with Antibody 1 with $IC_{50}$s of 0.3 nM and 0.5 nM, respectively (as discussed supra), which is comparable to the results seen with CSF-1. Therefore, IL-34 activity and its inhibition by Antibody 1 are similar to that seen with CSF-1.

IL-34 levels are elevated in many tumor cells including breast, prostate and endometrial tumor cell lines. Additionally, a subpopulation of prostate and breast patients have high IL-34 protein levels in their sera. Accordingly, since IL-34 functions nearly identically to CSF-1 and CSF-1 secretion is correlated to sensitivity of anti-CSF-1R treatments, elevated IL-34 levels also function as a sensitivity indicator or biomarker.

Breast Tumor Combination Studies

Inject Nu/nu mice (female, 7-8 weeks of age) subcutaneously with 1×10$^7$ HCC-1954 breast cells/mouse and allow tumors to reach 300 mm$^3$ before treatment. Randomize mice into groups of 12 and treat as follows:

TABLE 11

Breast Combination Studies

| Treatment | Dose | % T/C | Cohort Comparison | P value relative to control |
|---|---|---|---|---|
| 40 mpk Human IgG + 40 mpk Antibody 2 | TIW | 44 | 40 mpk Human IgG + 40 mpk Rat IgG control | 0.0002 |
| 40 mpk Herceptin ® + 40 mpk Rat IgG | TIW | 46 | 40 mpk Human IgG + 40 mpk Rat IgG control | <0.0001 |
| 40 mpk Herceptin ® + 40 mpk Antibody 2 | TIW | 26 | 40 mpk Human IgG + 40 mpk Rat IgG control | <0.0001 |
| 40 mg/kg Antibody 2 | TIW | 42 | saline control | 0.006 |
| 8 mg/kg IP Doxorubicin | Q7Dx2 | 50 | saline control | 0.008 |
| 40 mg/kg Antibody 2, 8 mg/kg Doxorubicin | TIW, Q7Dx2 | 28 | saline control | 0.0005 |
| 40 mg/kg Antibody 2 | TIW | 38 | saline control | <0.0001 |
| 10 mg/kg IP Paclitaxel | Q7Dx3 | 60 | saline control | <0.01 |
| 40 mg/kg Antibody 2, 10 mg/kg Paclitaxel | TIW, Q7Dx3 | 23 | saline control | <0.0001 |

TIW = Three time a week;
Q7Dx2 = once every seven days, twice;
Q7Dx3 = once every seven days, three times.

Measure tumor volumes and calculate the T/C % for each treatment group as the ratio of the relative tumor volumes versus the control group. Analyze tumor volumes using RM ANOVA.

In all the studies shown in Table 11, Antibody 2, Herceptin®, Doxorubicin and Paclitaxel inhibit tumor growth as single agents. However, combining Antibody 2 with a tumor-targeting agent has an additive effect indicating that a combination of an anti-CSF-1R antibody with chemotherapeutic or other agents that affect the tumor will be more efficacious than these reagents alone.

Prostate Tumor Combination Studies

Inject Nu/nu mice (male, 7-8 weeks of age) subcutaneously with 1.5×10$^7$ DU145 prostate cells/mouse and allow tumors to reach 300 mm$^3$ before treatment. Randomize mice into groups of 10 and treat as follows:

TABLE 12

Prostate Combination Study

| Treatment | Dose | % T/C | Cohort Comparison | P value relative to control |
|---|---|---|---|---|
| 40 mg/kg Antibody 2 | TIW | 50 | saline control | 0.03 |
| 12 mg/kg IP Docetaxel | Q7Dx3 | 59 | saline control | 0.15 |
| 40 mg/kg Antibody 2, 12 mg/kg Docetaxel | TIW, Q7Dx3 | 29 | saline control | <0.0001 |

TIW = Three time a week;
Q7Dx3 = once every seven days, three times.

Measure tumor volumes and calculate the T/C % for each treatment as the ratio of the relative tumor volumes versus the control group. Analyze tumor volumes using RM ANOVA.

Combining Antibody 2 with docetaxel has an additive effect indicating that combination with chemotherapeutics in prostate cancer will be more efficacious than chemotherapeutic reagents alone.

Additional Sequences

SEQ ID NO. 9

```
Gln Asp Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45
```

-continued

```
Ala Val Ile Trp Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Asp Tyr Glu Val Asp Tyr Gly Met Asp Val Trp Gly Gln
            100                 105                 110
Gly Thr Thr Val Thr Val Ala Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450
```

```
                                                      SEQ ID NO. 10
Ala Ile Gln Leu Thr Gln Ser Pro Ser Ser Leu Ser Ala Ser Val Gly
1               5                  10                  15

Asp Arg Val Thr Ile Thr Cys Arg Ala Ser Gln Gly Ile Ser Asn Ala
                20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Phe Asn Ser Tyr Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210

SEQ ID NO. 11
Met Gly Trp Ser Cys Ile Ile Leu Phe Leu Val Ala Thr Ala Thr Gly
1               5                  10                  15

Val His Ser Gln Asp Gln Leu Val Glu Ser Gly Gly Gly Val Val Gln
                20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Glu Gly Leu
    50                  55                  60

Glu Trp Val Ala Val Ile Trp Tyr Asp Gly Ser Asn Lys Tyr Tyr Ala
65              70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
                100                 105                 110

Tyr Tyr Cys Ala Arg Gly Asp Tyr Glu Val Asp Tyr Gly Met Asp Val
        115                 120                 125

Trp Gly Gln Gly Thr Thr Val Thr Val Ala Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190
```

-continued

```
Pro Ala Val Leu Gln Ser Ser Gly Leu Tyr Ser Leu Ser Ser Val Val
    195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

SEQ ID NO. 12
Met Gly Trp Ser Cys Ile Ile Leu Phe Leu Val Ala Thr Ala Thr Gly
1               5                   10                  15

Val His Ser Ala Ile Gln Leu Thr Gln Ser Pro Ser Ser Leu Ser Ala
                20                  25                  30

Ser Val Gly Asp Arg Val Thr Ile Thr Cys Arg Ala Ser Gln Gly Ile
            35                  40                  45

Ser Asn Ala Leu Ala Trp Tyr Gln Gln Lys Pro Gly Lys Ala Pro Lys
        50                  55                  60

Leu Leu Ile Tyr Asp Ala Ser Ser Leu Glu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Phe Asn Ser
            100                 105                 110

Tyr Pro Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140
```

```
Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

```
                                                          SEQ ID NO. 13
atgggatggt catgtatcat ccttttttctg gtagcaactg caactggagt acattcacag    60
gaccagctgg tggagtctgg gggaggcgtg gtccagcctg gaggtccct gagactctcc    120 tgtgcagcgt ctggattcac cttcagtagc tatggcatgc actgggtccg ccaggctcca    180 ggcgagggc tggagtgggt ggcagttata tggtatgatg aagtaataa atactatgca    240 gactccgtga agggccgatt caccatctcc agagacaatt ccaagaacac actgtatctg    300
caaatgaaca gcctgagagc cgaggacacg gctgtgtatt actgtgcgag aggtgactac    360
gaggtcgact acggaatgga cgtctggggc caagggacca cggtcaccgt cgcctcagct    420
agcaccaagg gcccatcggt cttccccctg gcaccctcct ccaagagcac ctctggggc    480 acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagagagt gagcccaaaa    720
tcttgtgaca aaactcacac atgcccaccg tgcccagcac ctgaactcct ggggggaccg    780
tcagtcttcc tcttccccc aaaacccaag gacaccctca tgatctcccg gacccctgag    840
gtcacatgcg tggtggtgga cgtgagccac gaagaccctg aggtcaagtt caactggtat    900
gtggacggcg tggaggtgca taatgccaag acaaagccgc gggaggagca gtacaacagc    960
acgtaccgtg tggtcagcgt cctcaccgtc ctgcaccaag actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aagtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctattcc aagctcaccg tggacaagag caggtggcag   1320
caggggaacg tcttctcatg ctccgtgatg catgaggctc tgcacaacca ctacacgcag   1380
aagagcctct ccctgtctcc gggcaaa                                        1407
```

```
                                                          SEQ ID NO. 14
atgggatggt catgtatcat ccttttttcta gtagcaactg caactggagt acattcagcc    60
atccagttga cccagtctcc atcctccctg tctgcatctg taggagacag agtcaccatc    120
acttgccggg caagtcaggg cattagcaat gctttagcct ggtatcagca gaaaccaggg    180
aaagctccta agctcctgat ctatgatgcc tccagtttgg aaagtgggt cccatcaagg    240 ttcagcggca gtggatctgg gacagatttc actctcacca tcagcagcct gcagcctgaa    300
gattttgcaa cttattactg tcaacagttt aatagttacc cgtggacgtt cggccaaggg    360
```

-continued

```
accaaggtgg aaatcaaacg tgagttctag aggatccatc tgggataagc atgctgtttt    420
ctgtctgtcc ctaacatgcc ctgtgattat ccgcaaacaa cacacccaag ggcagaactt    480
tgttacttaa acaccatcct gtttgcttct ttcctcagga actgtggctg caccatctgt    540
cttcatcttc ccgccatctg atgagcagtt gaaatctgga actgcctctg ttgtgtgcct    600
gctgaataac ttctatccca gagaggccaa agtacagtgg aaggtggata acgccctcca    660
atcgggtaac tcccaggaga gtgtcacaga gcaggacagc aaggacagca cctacagcct    720
cagcagcacc ctgacgctga gcaaagcaga ctacgagaaa cacaaagtct acgcctgcga    780
agtcacccat cagggcctga gctcgcccgt cacaaagagc ttcaacaggg gagagtgt     838
```

SEQ ID NO. 15

```
Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Ala Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335
```

-continued

Thr Tyr Leu Gly Pro Phe Ser Asp His Gln Pro Glu Pro Lys Leu Ala
    340                 345                 350

Asn Ala Thr Thr Lys Asp Thr Tyr Arg His Thr Phe Thr Leu Ser Leu
    355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

-continued

```
Leu Ala Ser Lys Asn Cys Ile His Arg Asp Val Ala Ala Arg Asn Val
770             775                 780

Leu Leu Thr Asn Gly His Val Ala Lys Ile Gly Asp Phe Gly Leu Ala
785             790                 795                 800

Arg Asp Ile Met Asn Asp Ser Asn Tyr Ile Val Lys Gly Asn Ala Arg
            805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865             870                 875                 880

Ala Pro Lys Asn Ile Tyr Ser Ile Met Gln Ala Cys Trp Ala Leu Glu
            885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Ser Glu Leu Glu Glu
930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
            965                 970
```

SEQ ID NO. 16

```
Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
            85                  90                  95

Ile His Leu Tyr Val Lys Asp Pro Ala Arg Pro Trp Asn Val Leu Ala
            100                 105                 110

Gln Glu Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
            165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
            210                 215                 220
```

```
Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
            245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
            325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
            370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
            405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
            435                 440                 445

Val Trp Asp Asp Pro Tyr Pro Glu Val Leu Ser Gln Glu Pro Phe His
            450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
            485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
            515                 520                 525

Leu Leu Leu Leu Leu Leu Leu Leu Leu Tyr Lys Tyr Lys Gln Lys Pro
            530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
            565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
            595                 600                 605

Ala Val Leu Lys Val Ala Val Lys Met Leu Lys Ser Thr Ala His Ala
            610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
            645                 650                 655
```

-continued

```
Gly Pro Val Leu Val Ile Thr Glu Tyr Cys Cys Tyr Gly Asp Leu Leu
        660                 665                 670

Asn Phe Leu Arg Arg Lys Ala Glu Ala Met Leu Gly Pro Ser Leu Ser
    675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
            725                 730                 735

Phe Ser Glu Gln Asp Leu Asp Lys Glu Asp Gly Arg Pro Leu Glu Leu
        740                 745                 750

Arg Asp Leu Leu His Phe Ser Ser Gln Val Ala Gln Gly Met Ala Phe
    755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
            805                 810                 815

Leu Pro Val Lys Trp Met Ala Pro Glu Ser Ile Phe Asp Cys Val Tyr
        820                 825                 830

Thr Val Gln Ser Asp Val Trp Ser Tyr Gly Ile Leu Leu Trp Glu Ile
    835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
            885                 890                 895

Pro Thr His Arg Pro Thr Phe Gln Gln Ile Cys Ser Phe Leu Gln Glu
        900                 905                 910

Gln Ala Gln Glu Asp Arg Arg Glu Arg Asp Tyr Thr Asn Leu Pro Ser
    915                 920                 925

Ser Ser Arg Ser Gly Gly Ser Gly Ser Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
            965                 970

SEQ ID NO. 17
Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
            85                  90                  95
```

-continued

```
Met Arg Phe Arg Asp Asn Thr Pro Asn Ala Ile Ala Ile Val Gln Leu
    100                 105                 110

Gln Glu Leu Ser Leu Arg Leu Lys Ser Cys Phe Thr Lys Asp Tyr Glu
    115                 120                 125

Glu His Asp Lys Ala Cys Val Arg Thr Phe Tyr Glu Thr Pro Leu Gln
    130                 135             140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
            165                 170                 175

Glu Cys Ser Ser Gln Asp Val Val Thr Lys Pro Asp Cys Asn Cys Leu
        180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
            245                 250                 255

Thr Cys Gln Ser Phe Glu Pro Pro Glu Thr Pro Val Val Lys Asp Ser
        260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
            325                 330                 335

Pro Ala Arg Pro Ser Asn Phe Leu Ser Ala Ser Ser Pro Leu Pro Ala
        340                 345                 350

Ser Ala Lys Gly Gln Gln Pro Ala Asp Val Thr Gly Thr Ala Leu Pro
        355                 360                 365

Arg Val Gly Pro Val Arg Pro Thr Gly Gln Asp Trp Asn His Thr Pro
    370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
            405                 410                 415

Ser Thr Leu Ser Ala Gln Pro Gln Leu Ser Arg Ser His Ser Ser Gly
        420                 425                 430

Ser Val Leu Pro Leu Gly Glu Leu Glu Gly Arg Arg Ser Thr Arg Asp
    435                 440                 445

Arg Arg Ser Pro Ala Glu Pro Glu Gly Gly Pro Ala Ser Glu Gly Ala
    450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Phe Ser Pro Gln Leu Gln Glu Ser
            485                 490                 495

Val Phe His Leu Leu Val Pro Ser Val Ile Leu Val Leu Leu Ala Val
        500                 505                 510

Gly Gly Leu Leu Phe Tyr Arg Trp Arg Arg Arg Ser His Gln Glu Pro
    515                 520                 525
```

-continued

```
Gln Arg Ala Asp Ser Pro Leu Glu Gln Pro Glu Gly Ser Pro Leu Thr
530                 535                 540

Gln Asp Asp Arg Gln Val Glu Leu Pro Val
545                 550
```

SEQ ID NO. 18

```
Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
                20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
                100                 105                 110

His Pro Ser Trp Lys Tyr Leu Gln Glu Val Glu Thr Leu Leu Leu Asn
            115                 120                 125

Val Gln Gln Gly Leu Thr Asp Val Glu Val Ser Pro Lys Val Glu Ser
130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
        195                 200                 205

Ala Thr Gln Leu Tyr Pro Pro Pro Trp Ser Pro Ser Ser Pro Pro
    210                 215                 220

His Ser Thr Gly Ser Val Arg Pro Val Arg Ala Gln Gly Glu Gly Leu
225                 230                 235                 240

Leu Pro
```

We claim:

1. An antibody, or fragment thereof, that specifically binds human CSF-1R variant (SEQ ID NO. 15), comprising a CDRH1 comprising the sequence SYGMH (SEQ ID NO:1), a CDRH2 comprising the sequence VIWYDGSNKYYADS-VKG (SEQ ID NO:2), a CDRH3 comprising the sequence GDYEVDYGMDV (SEQ ID NO:3), a CDRL1 comprising the sequence RASQGISNALA (SEQ ID NO:4), a CDRL2 comprising the sequence DASSLES (SEQ ID NO:5), and a CDRL3 comprising the sequence QQFNSYPWT (SEQ ID NO:6).

2. The antibody, or fragment thereof, of claim 1, comprising a VL comprising the amino acid sequence:

(SEQ ID NO: 8)
AIQLTQSPSSLSASVGDRVTITCRASQGISNALAWYQQKPGKAPKLLI

YDASSLESGVPSRFSGSGSGTDFTLTISSLQPEDFATYYCQQFNSYPW

TFGQGTKVEIK, and a VH comprising the amino acid sequence:

(SEQ ID NO: 7)
QDQLVESGGGVVQPGRSLRLSCAASGFTFSSYGMHWVRQAPGEGLEWV

AVIWYDGSNKYYADSVKGRFTISRDNSKNTLYLQMNSLRAEDTAVYYC

ARGDYEVDYGMDVWGQGTTVTVAS.

3. The antibody, or fragment thereof, of claim 2, comprising a heavy chain comprising the amino acid sequence of SEQ ID NO:9 and a light chain comprising the amino acid sequence of SEQ ID NO:10.

4. The antibody, or fragment thereof, of claim 3 comprising two heavy chains, each comprising the amino acid sequence of SEQ ID NO:9 and two light chains, each comprising the amino acid sequence of SEQ ID NO:10.

5. A pharmaceutical composition comprising the antibody or fragment of claim 1 together with a pharmaceutically acceptable carrier, diluent or excipient.

6. A pharmaceutical composition of claim 5 further comprising an additional pharmaceutical agent.

7. A method of treating cancer in a mammal, comprising administering to said mammal in need thereof an effective amount of an antibody or fragment thereof of claim 1, wherein the cancer is selected from the group consisting of leukemia, breast cancer, endometrial cancer, prostate cancer, ovarian cancer, colorectal cancer, hepatocellular cancer, renal cancer, multiple myeloma, and hodgkin's lymphoma.

8. The method of claim 7, wherein the cancer is selected from the group consisting of leukemia, breast cancer, endometrial cancer, and prostate cancer.

9. The method of claim 8, wherein the cancer is selected from the group consisting of leukemia, breast cancer, and prostate cancer.

10. The method of claim 7, further comprising administering another anti-cancer treatment to said mammal wherein said anti-cancer treatment is selected from the group consisting of an anti-angiogenesis agent, a chemotherapeutic agent, and an anti-neoplastic agent.

11. The method of claim 10, wherein said anti-neoplastic agent is selected from the group consisting of docetaxel, paclitaxel, Herceptin® and doxorubicin.

12. A method of treating cancer in a patient, comprising the steps: (1) measuring the level of CSF-1 in a sample taken from the patient wherein the sample is selected from the group consisting of blood, serum or plasma, and (2) administering to the patient the antibody or fragment thereof according to claim 1 if the CSF-1 levels are higher than CSF-1 levels found in blood, serum or plasma in a control population of individuals that have not been diagnosed as having a cancerous condition or signs of infection.

13. A method of treating cancer in a patient, comprising the steps: (1) measuring the level of IL-34 in a sample taken from the patient wherein the sample is selected from the group consisting of blood, serum or plasma, and (2) administering to the patient the antibody or fragment thereof according to claim 1 if the IL-34 levels are higher than IL-34 levels found in blood, serum or plasma in a control population of individuals that have not been diagnosed as having a cancerous condition or signs of infection.

* * * * *